US011583488B2

(12) United States Patent
Zhang et al.

(10) Patent No.: US 11,583,488 B2
(45) Date of Patent: Feb. 21, 2023

(54) METHOD OF IMPROVING PENETRATION OF A VITAMIN B3 COMPOUND INTO SKIN

(71) Applicant: The Procter & Gamble Company, Cincinnati, OH (US)

(72) Inventors: Lu Zhang, Singapore (SG); Peter Brendan Styczynski, West Chester, OH (US); Sudeep Chakravarty, Singapore (SG); Joseph Michael Zukowski, Blue Ash, OH (US); Chuiying Li, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 32 days.

(21) Appl. No.: 17/335,674

(22) Filed: Jun. 1, 2021

(65) Prior Publication Data

US 2021/0369588 A1    Dec. 2, 2021

Related U.S. Application Data

(60) Provisional application No. 63/033,033, filed on Jun. 1, 2020.

(51) Int. Cl.
| | | |
|---|---|---|
| *A61K 8/67* | (2006.01) | |
| *A61K 8/06* | (2006.01) | |
| *A61K 8/365* | (2006.01) | |
| *A61Q 19/00* | (2006.01) | |
| *A61Q 17/04* | (2006.01) | |
| *A61Q 19/02* | (2006.01) | |
| *A61Q 19/08* | (2006.01) | |
| *A61Q 19/10* | (2006.01) | |

(52) U.S. Cl.
CPC .............. *A61K 8/675* (2013.01); *A61K 8/06* (2013.01); *A61K 8/365* (2013.01); *A61Q 19/00* (2013.01); *A61K 2800/48* (2013.01); *A61K 2800/884* (2013.01); *A61Q 17/04* (2013.01); *A61Q 19/007* (2013.01); *A61Q 19/008* (2013.01); *A61Q 19/02* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,755,560 A | 8/1973 | Dickert et al. |
| 3,856,941 A | 12/1974 | Turner |
| 3,859,436 A | 1/1975 | Jacobi |
| 3,867,549 A | 2/1975 | Costello |
| 3,892,853 A | 7/1975 | Cobble |
| 4,007,266 A | 2/1977 | Choay |
| 4,178,372 A | 12/1979 | Coats |
| 4,406,884 A | 9/1983 | Fawzi |
| 4,421,769 A | 12/1983 | Dixon et al. |
| 4,481,187 A | 11/1984 | Kondo |
| 4,485,091 A | 11/1984 | Fitton |
| 4,792,443 A | 12/1988 | Filomeno |
| 4,879,107 A | 11/1989 | Vanlerberghe |
| 4,923,977 A | 5/1990 | Lang |
| 4,981,845 A | 1/1991 | Pereira |
| 5,053,230 A | 10/1991 | Gazzani |
| 5,140,043 A | 8/1992 | Darr |
| 5,229,104 A | 7/1993 | Sottery |
| 5,302,376 A | 4/1994 | Forestier |
| 5,346,694 A | 9/1994 | Juneja |
| 5,419,896 A | 5/1995 | Bimczok |
| 5,429,815 A | 7/1995 | Faryniarz |
| 5,496,538 A | 3/1996 | Zimmerman |
| 5,520,918 A | 5/1996 | Smith |
| 5,549,886 A | 8/1996 | Grollier |
| 5,549,888 A | 8/1996 | Venkateswaran |
| 5,567,427 A | 10/1996 | Papadakis |
| 5,607,921 A | 3/1997 | Bernard |
| 5,616,332 A | 4/1997 | Herstein |
| 5,629,004 A | 5/1997 | Candau |
| 5,654,341 A | 8/1997 | Struewing |
| 5,707,635 A | 1/1998 | Deckner |
| 5,718,906 A | 2/1998 | Martin |

(Continued)

FOREIGN PATENT DOCUMENTS

| | | |
|---|---|---|
| AU | 2005293830 B2 | 10/2010 |
| AU | 2016206278 A1 | 2/2017 |

(Continued)

OTHER PUBLICATIONS

PCT Search Report and Written Opinion for PCT/US2021/035140 dated Nov. 24, 2021.

(Continued)

*Primary Examiner* — Nicole P Babson
(74) *Attorney, Agent, or Firm* — Alexandra S. Anoff

(57) ABSTRACT

Disclosed is a method of improving the penetration of a vitamin $B_3$ compound into skin. The method involves a skin care regimen in which at least two skin care compositions are used in sequence to treat a target portion of skin where a skin health or appearance benefit is desired. The first composition applied to the skin is a low-pH skin care composition that contains a first concentration of a vitamin $B_3$ compound. The second skin care composition applied to the skin is a conventional skin care composition that contains a higher concentration of the vitamin $B_3$ compound than the first composition. When applied in the proper sequence, the regimen results in an unexpectedly high vitamin $B_3$ flux into the skin.

20 Claims, 3 Drawing Sheets

(56) References Cited

U.S. PATENT DOCUMENTS

| | | |
|---|---|---|
| 5,718,908 A | 2/1998 | Fanelli |
| 5,736,128 A | 4/1998 | Chaudhuri |
| 5,759,558 A | 6/1998 | Epstein |
| 5,824,666 A | 10/1998 | Deckner |
| 5,833,998 A | 11/1998 | Biedermann et al. |
| 5,871,764 A | 2/1999 | Diaz |
| 5,872,112 A | 2/1999 | Blank |
| 5,876,736 A | 3/1999 | Cohen |
| 5,939,082 A | 8/1999 | Oblong et al. |
| 5,961,999 A | 10/1999 | Bimczok |
| 5,968,528 A | 10/1999 | Deckner et al. |
| 5,972,359 A | 10/1999 | Sine et al. |
| 5,989,536 A | 11/1999 | Deckner |
| 5,993,832 A | 11/1999 | Lorant |
| 6,001,379 A | 12/1999 | Griat |
| 6,042,813 A | 3/2000 | Fowler |
| 6,045,779 A | 4/2000 | Mueller |
| 6,099,825 A | 8/2000 | Mcshane |
| 6,153,176 A | 11/2000 | Kaleta |
| 6,174,533 B1 | 1/2001 | SaNogueira, Jr. et al. |
| 6,217,887 B1 | 4/2001 | Beerse |
| 6,218,347 B1 | 4/2001 | Rau |
| 6,224,888 B1 | 5/2001 | Vatter et al. |
| 6,238,678 B1 | 5/2001 | Oblong et al. |
| 6,261,541 B1 | 7/2001 | Karpov |
| 6,281,203 B1 | 8/2001 | Touzan |
| 6,287,582 B1 | 9/2001 | Gott |
| 6,287,583 B1 | 9/2001 | Warren |
| 6,299,885 B1 | 10/2001 | Yamasaki |
| H2013 H | 2/2002 | Boyd et al. |
| 6,387,918 B1 | 5/2002 | Yamanaka |
| 6,410,039 B1 | 6/2002 | Walker |
| 6,416,768 B1 | 7/2002 | Ravaux |
| 6,419,907 B1 | 7/2002 | Hocquaux |
| 6,432,415 B1 | 8/2002 | Osborne |
| 6,440,432 B1 | 8/2002 | Mukherjee |
| 6,440,437 B1 | 8/2002 | Krzysik et al. |
| 6,461,622 B2 | 10/2002 | Liu |
| 6,468,549 B1 | 10/2002 | Dupuis |
| 6,492,326 B1 | 12/2002 | Robinson |
| 6,524,598 B2 | 2/2003 | Sunkel |
| 6,585,984 B1 | 7/2003 | Scott |
| 6,589,514 B2 | 7/2003 | Jensen et al. |
| 6,632,444 B1 | 10/2003 | Zhou |
| 6,638,519 B1 | 10/2003 | Lorant |
| 6,682,750 B2 | 1/2004 | Loeffler |
| 6,696,049 B2 | 2/2004 | Vatter et al. |
| 6,706,259 B1 | 3/2004 | Gardner |
| 6,759,051 B2 | 7/2004 | Saint-leger |
| 6,831,107 B2 | 12/2004 | Dederen |
| 6,903,210 B2 | 6/2005 | Behrends |
| 6,906,106 B2 | 6/2005 | Chevalier |
| 6,932,976 B2 | 8/2005 | Brooks |
| 6,979,452 B2 | 12/2005 | Zhou |
| 6,986,895 B2 | 1/2006 | Suares |
| 7,018,660 B2 | 3/2006 | Murad |
| 7,176,191 B2 | 2/2007 | Dale |
| 7,179,771 B1 | 2/2007 | Charlton |
| 7,291,351 B2 | 11/2007 | Azik |
| 7,300,678 B2 | 11/2007 | Paufique |
| 7,332,152 B2 | 2/2008 | Sanzgiri |
| 7,378,083 B2 | 5/2008 | Stephens |
| 7,416,719 B2 | 8/2008 | Huerta |
| 7,455,849 B2 | 11/2008 | Utschig |
| 7,741,366 B2 | 6/2010 | Mackles |
| 7,799,356 B2 | 9/2010 | Raschke |
| 7,815,900 B1 | 10/2010 | Cannell et al. |
| 7,829,107 B2 | 11/2010 | Popp |
| 8,063,097 B2 | 11/2011 | Robinson |
| 8,106,184 B2 | 1/2012 | Sauve |
| 8,197,807 B2 | 6/2012 | Brenner |
| 8,293,279 B2 | 10/2012 | Schiffer |
| 8,293,784 B2 | 10/2012 | Rudolph |
| 8,329,758 B2 | 12/2012 | Ali |
| 8,343,902 B2 | 1/2013 | Walters |
| 8,383,086 B2 | 2/2013 | Brenner |
| 8,435,950 B2 | 5/2013 | Dal |
| 8,475,851 B2 | 7/2013 | Herrmann |
| 8,491,464 B2 | 7/2013 | Yokoi |
| 8,529,920 B2 | 9/2013 | Liu |
| 8,529,979 B2 | 9/2013 | Abril |
| 8,546,364 B2 | 10/2013 | Patel |
| 8,652,447 B2 | 2/2014 | Maesen |
| 8,828,410 B2 | 9/2014 | Sakuta |
| 8,883,215 B2 | 11/2014 | Beck |
| 8,895,034 B2 | 11/2014 | Bennett |
| 8,895,513 B2 | 11/2014 | Trudsoe |
| 8,911,774 B2 | 12/2014 | Giampapa |
| 8,933,217 B2 | 1/2015 | Rinsch |
| 8,968,755 B2 | 3/2015 | Schlessinger |
| 8,999,923 B2 | 4/2015 | Cao et al. |
| 9,034,833 B1 | 5/2015 | Chiou et al. |
| 9,068,148 B2 | 6/2015 | Tamareselvy |
| 9,084,734 B2 | 7/2015 | Collier |
| 9,186,304 B2 | 11/2015 | Claas |
| 9,271,912 B2 | 3/2016 | Fernandez Prieto et al. |
| 9,283,163 B2 | 3/2016 | Santhanam |
| 9,339,447 B2 | 5/2016 | Souzy |
| 9,364,414 B2 | 6/2016 | Domloge |
| 9,364,690 B2 | 6/2016 | Lorant |
| 9,381,144 B1 | 7/2016 | Hilt |
| 9,446,265 B2 | 9/2016 | Jansen et al. |
| 9,468,597 B1 | 10/2016 | Perry |
| 9,474,699 B2 | 10/2016 | Sun |
| 9,486,394 B2 | 11/2016 | Abram |
| 9,526,690 B2 | 12/2016 | Da Costa Pereira |
| 9,655,934 B2 | 5/2017 | Schiemann |
| 9,775,789 B2 | 10/2017 | Simmons |
| 9,795,544 B2 | 10/2017 | Lorant |
| 9,820,482 B2 | 11/2017 | Bingham |
| 9,833,398 B2 | 12/2017 | Hakozaki |
| 9,834,635 B2 | 12/2017 | Klug |
| 9,867,774 B1 | 1/2018 | Hakim |
| 9,895,300 B2 | 2/2018 | Schroeder |
| 9,949,902 B2 | 4/2018 | Mundschau |
| 10,124,030 B2 | 11/2018 | Goldsberry |
| 10,130,578 B2 | 11/2018 | Brillouet |
| 10,363,209 B2 | 7/2019 | Wu |
| 10,398,640 B2 | 9/2019 | Widgerow |
| 10,413,485 B2 | 9/2019 | Huang |
| 10,441,822 B2 | 10/2019 | Buckley |
| 10,449,126 B2 | 10/2019 | L'alloret |
| 10,660,838 B2 | 5/2020 | Hakozaki |
| 10,959,933 B1 | 3/2021 | Zhang et al. |
| 2001/0009671 A1 | 7/2001 | Helbiche |
| 2001/0024655 A1 | 9/2001 | Schneider |
| 2002/0022040 A1 | 2/2002 | Robinson et al. |
| 2002/0022052 A1 | 2/2002 | Dransfield |
| 2002/0042438 A1 | 4/2002 | Pelletier |
| 2002/0058704 A1 | 5/2002 | Malik |
| 2002/0168423 A1 | 11/2002 | Wurzburger |
| 2002/0193264 A1 | 12/2002 | Cannell et al. |
| 2003/0032617 A1 | 2/2003 | Harel et al. |
| 2003/0049212 A1 | 3/2003 | Robinson et al. |
| 2003/0091603 A1 | 5/2003 | Ohmori |
| 2003/0118620 A1 | 6/2003 | Zhang |
| 2003/0147968 A1 | 8/2003 | Farber |
| 2003/0158363 A1 | 8/2003 | Nakanishi |
| 2003/0165552 A1 | 9/2003 | Fox |
| 2003/0223982 A1 | 12/2003 | Schlotmann |
| 2004/0013784 A1 | 1/2004 | Costa |
| 2004/0028634 A1 | 2/2004 | Tanaka |
| 2004/0081672 A1 | 4/2004 | Gupta |
| 2004/0092482 A1 | 5/2004 | Gupta |
| 2004/0175347 A1 | 9/2004 | Bissett |
| 2004/0265268 A1 | 12/2004 | Jain |
| 2005/0008601 A1 | 1/2005 | Ariotto |
| 2005/0037036 A1 | 2/2005 | Nielsen |
| 2005/0100519 A1 | 5/2005 | Guth |
| 2005/0106194 A1 | 5/2005 | Schiltz |
| 2005/0170013 A1 | 8/2005 | Douglas |
| 2005/0176677 A1 | 8/2005 | Dal Farra et al. |
| 2005/0227327 A1 | 10/2005 | Brenner |
| 2005/0244348 A1 | 11/2005 | Lindemann |

(56) References Cited

U.S. PATENT DOCUMENTS

| | | |
|---|---|---|
| 2005/0267023 A1 | 12/2005 | Sinclair et al. |
| 2006/0018861 A1 | 1/2006 | Chen et al. |
| 2006/0034875 A1 | 2/2006 | Nakanishi et al. |
| 2006/0040851 A1 | 2/2006 | Ghosh |
| 2006/0127426 A1 | 6/2006 | Ross |
| 2006/0147508 A1 | 7/2006 | Gupta |
| 2006/0161121 A1 | 7/2006 | Klaveness |
| 2006/0165741 A1 | 7/2006 | Coffindaffer |
| 2006/0210499 A1 | 9/2006 | Hoeffkes |
| 2006/0229265 A1 | 10/2006 | Milburn et al. |
| 2006/0275237 A1 | 12/2006 | Bissett et al. |
| 2007/0027095 A1 | 2/2007 | Brenner |
| 2007/0196344 A1 | 8/2007 | Osborne et al. |
| 2007/0231288 A1 | 10/2007 | Arnaud et al. |
| 2007/0232508 A1 | 10/2007 | Oshimura |
| 2007/0232687 A1 | 10/2007 | Kato |
| 2008/0025932 A1 | 1/2008 | Bissett et al. |
| 2008/0057138 A1 | 3/2008 | Telford |
| 2008/0181956 A1 | 7/2008 | Ha |
| 2008/0206169 A1 | 8/2008 | Millikin |
| 2008/0206373 A1 | 8/2008 | Millikin |
| 2008/0247960 A1 | 10/2008 | Yuan |
| 2008/0287533 A1 | 11/2008 | Gupta |
| 2008/0312169 A1 | 12/2008 | Johnson et al. |
| 2008/0312181 A1 | 12/2008 | Harel et al. |
| 2008/0317795 A1 | 12/2008 | Traynor |
| 2009/0068219 A1 | 3/2009 | Elie |
| 2009/0196942 A1 | 8/2009 | Goyarts et al. |
| 2009/0197819 A1 | 8/2009 | Johnson et al. |
| 2009/0214628 A1 | 8/2009 | De |
| 2009/0215723 A1 | 8/2009 | Le |
| 2009/0232750 A1 | 9/2009 | St. Cyr |
| 2009/0317354 A1 | 12/2009 | Nishimura |
| 2010/0015072 A1 | 1/2010 | Polla et al. |
| 2010/0040608 A1 | 2/2010 | Wahren-Herlenius et al. |
| 2010/0092408 A1 | 4/2010 | Breyfogle et al. |
| 2010/0092412 A1 | 4/2010 | Gohier |
| 2010/0105638 A1 | 4/2010 | Den-braven |
| 2010/0183531 A1 | 7/2010 | Johncock |
| 2010/0189669 A1 | 7/2010 | Hakozaki |
| 2010/0203175 A1 | 8/2010 | Abdul-malak |
| 2010/0204323 A1 | 8/2010 | Theiler |
| 2010/0215726 A1 | 8/2010 | Roth |
| 2010/0239510 A1 | 9/2010 | Ha |
| 2010/0254919 A1 | 10/2010 | Bommarito |
| 2010/0272667 A1 | 10/2010 | Kyte, III et al. |
| 2010/0291190 A1 | 11/2010 | Giampapa |
| 2011/0097286 A1 | 4/2011 | Swanson |
| 2011/0101021 A1 | 5/2011 | Greer et al. |
| 2011/0117219 A1 | 5/2011 | Springer |
| 2011/0123467 A1 | 5/2011 | Roth |
| 2011/0152384 A1 | 6/2011 | Gunn |
| 2011/0158920 A1 | 6/2011 | Morley |
| 2011/0172160 A1 | 7/2011 | Cao |
| 2011/0229427 A1 | 9/2011 | Klug |
| 2011/0262025 A1 | 10/2011 | Jarrold et al. |
| 2011/0262560 A1 | 10/2011 | Dabe et al. |
| 2012/0003168 A1 | 1/2012 | Lyga et al. |
| 2012/0022013 A1 | 1/2012 | Sinclair et al. |
| 2012/0039967 A1 | 2/2012 | Lou |
| 2012/0093896 A1 | 4/2012 | Mongiat |
| 2012/0121534 A1 | 5/2012 | Thorel et al. |
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0172584 A1 | 7/2012 | Sauve et al. |
| 2012/0189684 A1 | 7/2012 | Buckley |
| 2012/0197016 A1 | 8/2012 | Laughlin, II et al. |
| 2012/0225050 A1 | 9/2012 | Knight et al. |
| 2013/0022557 A1 | 1/2013 | Swanson |
| 2013/0125317 A1 | 5/2013 | Rudolph |
| 2013/0164234 A1 | 6/2013 | Gruber |
| 2013/0164265 A1 | 6/2013 | Flavin |
| 2013/0189211 A1 | 7/2013 | Marini |
| 2013/0295024 A1 | 11/2013 | Hammer |
| 2013/0319449 A1 | 12/2013 | Xavier et al. |
| 2014/0020701 A1 | 1/2014 | Galderisi |
| 2014/0065099 A1 | 3/2014 | Alvarez et al. |
| 2014/0090660 A1 | 4/2014 | Xavier et al. |
| 2014/0127332 A1 | 5/2014 | Bitler |
| 2014/0158148 A1 | 6/2014 | Mette |
| 2014/0170195 A1 | 6/2014 | Fassih et al. |
| 2014/0190507 A9 | 7/2014 | Xavier et al. |
| 2014/0328774 A1 | 11/2014 | Rout et al. |
| 2014/0328775 A1 | 11/2014 | Laughlin, II et al. |
| 2014/0336308 A1 | 11/2014 | Mateu et al. |
| 2014/0369943 A1 | 12/2014 | Pilz |
| 2015/0065476 A1 | 3/2015 | Aistrup |
| 2015/0118169 A1 | 4/2015 | Hakozaki et al. |
| 2015/0164941 A1 | 6/2015 | Munisekhar |
| 2015/0196464 A1 | 7/2015 | Jansen et al. |
| 2015/0209261 A1 | 7/2015 | Ross |
| 2015/0209272 A1 | 7/2015 | Weisman |
| 2015/0272860 A1 | 10/2015 | Mette |
| 2015/0272865 A1 | 10/2015 | Mette |
| 2015/0359723 A1 | 12/2015 | Kim |
| 2016/0000692 A1 | 1/2016 | Zamyatin et al. |
| 2016/0074643 A1 | 3/2016 | Mcildowie et al. |
| 2016/0077080 A1 | 3/2016 | Laughlin, II et al. |
| 2016/0089324 A1 | 3/2016 | Nijakowski |
| 2016/0095806 A1 | 4/2016 | Farber |
| 2016/0102179 A1 | 4/2016 | Wagner |
| 2016/0128944 A1 | 5/2016 | Chawrai |
| 2016/0151270 A1 | 6/2016 | Brooks |
| 2016/0199404 A1 | 7/2016 | Blotsky |
| 2016/0235646 A1 | 8/2016 | Shah et al. |
| 2016/0250134 A1 | 9/2016 | Castle |
| 2016/0250241 A1 | 9/2016 | Deren-Lewis et al. |
| 2016/0317418 A1 | 11/2016 | Hakazaki et al. |
| 2016/0317419 A1 | 11/2016 | Hakazaki et al. |
| 2016/0317420 A1 | 11/2016 | Hakazaki et al. |
| 2016/0374908 A1 | 12/2016 | Hakozaki et al. |
| 2016/0374918 A1 | 12/2016 | Dihora et al. |
| 2016/0374919 A1 | 12/2016 | Hakozaki et al. |
| 2017/0079408 A1 | 3/2017 | Lee |
| 2017/0121746 A1 | 5/2017 | Velasquez et al. |
| 2017/0165160 A1 | 6/2017 | Schulze Zur Wiesche |
| 2017/0172972 A1 | 6/2017 | Buge |
| 2017/0196795 A1 | 7/2017 | Hakozaki |
| 2017/0227011 A1 | 8/2017 | Zhou et al. |
| 2017/0266099 A1 | 9/2017 | Kroon |
| 2017/0333321 A1 | 11/2017 | Carnali |
| 2017/0360674 A1 | 12/2017 | Schulze Zur Wiesche |
| 2018/0015013 A1 | 1/2018 | Prendergast |
| 2018/0042840 A1 | 2/2018 | Almiñana Domènech |
| 2018/0104175 A1 | 4/2018 | Liu |
| 2018/0140518 A1 | 5/2018 | Deckner |
| 2018/0177703 A1 | 6/2018 | Perricone |
| 2018/0185283 A1 | 7/2018 | Buge |
| 2018/0271760 A1 | 9/2018 | Baca |
| 2018/0271881 A1 | 9/2018 | Buge |
| 2018/0280297 A1 | 10/2018 | Buge |
| 2018/0280298 A1 | 10/2018 | Buge |
| 2018/0311137 A1 | 11/2018 | Mckiernan |
| 2018/0344624 A1 | 12/2018 | Athwal |
| 2018/0369110 A1 | 12/2018 | Hakozaki |
| 2019/0021961 A1 | 1/2019 | Abels |
| 2019/0076811 A1 | 3/2019 | Lei |
| 2019/0125654 A1 | 5/2019 | Goldsberry |
| 2019/0240141 A1 | 8/2019 | Boland |
| 2019/0328631 A1 | 10/2019 | Lou |
| 2019/0380945 A1 | 12/2019 | Hakozaki |
| 2020/0002377 A1 | 1/2020 | Van Den Nest |
| 2020/0009123 A1 | 1/2020 | Hakozaki |
| 2020/0253851 A1 | 8/2020 | Hakozaki |

FOREIGN PATENT DOCUMENTS

| | | |
|---|---|---|
| BR | 102013005446 A2 | 6/2015 |
| CA | 2517765 C | 7/2009 |
| CA | 2217032 C | 12/2009 |
| CH | 711092 A2 | 11/2016 |
| CN | 1261780 A | 8/2000 |
| CN | 101182299 A | 5/2008 |

(56) References Cited

FOREIGN PATENT DOCUMENTS

| | | |
|---|---|---|
| CN | 100418507 C | 9/2008 |
| CN | 100457074 C | 2/2009 |
| CN | 101048375 B | 12/2012 |
| CN | 103070781 A | 5/2013 |
| CN | 103211717 A | 7/2013 |
| CN | 102670469 B | 10/2013 |
| CN | 103565721 A | 2/2014 |
| CN | 102871863 B | 4/2014 |
| CN | 102716511 B | 5/2014 |
| CN | 104274340 A | 1/2015 |
| CN | 104688617 A | 6/2015 |
| CN | 104688654 A | 6/2015 |
| CN | 104784084 A | 7/2015 |
| CN | 104812363 A | 7/2015 |
| CN | 104873436 A | 9/2015 |
| CN | 104983630 A | 10/2015 |
| CN | 105168677 A | 12/2015 |
| CN | 104168883 B | 5/2016 |
| CN | 105769747 A | 7/2016 |
| CN | 103987372 B | 8/2016 |
| CN | 104095770 B | 8/2016 |
| CN | 105997548 A | 10/2016 |
| CN | 106214607 A | 12/2016 |
| CN | 106456476 A | 2/2017 |
| CN | 106729669 A | 5/2017 |
| CN | 106821849 A | 6/2017 |
| CN | 107137299 A | 9/2017 |
| CN | 107320355 A | 11/2017 |
| CN | 107427429 A | 12/2017 |
| CN | 108078889 A | 5/2018 |
| CN | 105640870 B | 12/2018 |
| CN | 108938445 A | 12/2018 |
| CN | 109010216 A | 12/2018 |
| CN | 109106806 A | 1/2019 |
| DE | 1949740 A1 | 7/1970 |
| DE | 2423637 A1 | 11/1975 |
| DE | 3029263 A1 | 3/1981 |
| DE | 10063658 A1 | 7/2002 |
| DE | 10063660 A1 | 7/2002 |
| DE | 10139582 A1 | 2/2003 |
| DE | 20220609 U1 | 12/2003 |
| DE | 60104036 T2 | 8/2004 |
| DE | 202004006865 U1 | 12/2004 |
| DE | 69828095 T2 | 1/2005 |
| DE | 102004008440 A1 | 9/2005 |
| DE | 102004035737 A1 | 3/2006 |
| DE | 60030917 T2 | 11/2006 |
| DE | 60032597 T2 | 2/2007 |
| DE | 19712980 B4 | 10/2008 |
| DE | 102007036499 A1 | 2/2009 |
| DE | 102007037432 A1 | 2/2009 |
| DE | 102008010921 A1 | 9/2009 |
| DE | 102010026465 A1 | 5/2011 |
| DE | 102010027180 A1 | 5/2011 |
| DE | 102011084904 A1 | 6/2012 |
| DE | 102011087883 A1 | 8/2012 |
| DE | 102011089357 A1 | 8/2012 |
| DE | 102011089612 A1 | 6/2013 |
| DE | 102013225182 A1 | 4/2014 |
| EP | 0134483 A2 | 3/1985 |
| EP | 0315541 A1 | 5/1989 |
| EP | 0350275 A3 | 6/1991 |
| EP | 0826366 A3 | 4/1998 |
| EP | 0995427 A3 | 5/2000 |
| EP | 1417954 A1 | 5/2004 |
| EP | 1459736 A1 | 9/2004 |
| EP | 1618867 A1 | 1/2006 |
| EP | 1815843 A2 | 8/2007 |
| EP | 1949887 A2 | 7/2008 |
| EP | 1779845 B1 | 10/2010 |
| EP | 1997537 A3 | 2/2012 |
| EP | 2020227 B1 | 8/2012 |
| EP | 2548549 A1 | 1/2013 |
| EP | 2033622 B1 | 3/2013 |
| EP | 1276513 B1 | 11/2013 |
| EP | 2057980 B1 | 4/2014 |
| EP | 1435771 B1 | 7/2015 |
| EP | 1609462 B1 | 7/2015 |
| EP | 3040065 A1 | 7/2016 |
| EP | 2793828 B1 | 8/2016 |
| EP | 3050900 A1 | 8/2016 |
| EP | 1776161 B1 | 10/2016 |
| EP | 1852102 B1 | 10/2016 |
| EP | 1904020 B1 | 10/2016 |
| EP | 2308456 B1 | 10/2016 |
| EP | 1786893 B2 | 11/2016 |
| EP | 1672037 B1 | 12/2016 |
| EP | 1813255 B1 | 11/2017 |
| EP | 1475080 B1 | 4/2018 |
| EP | 2263788 B1 | 7/2018 |
| EP | 3220883 B1 | 7/2018 |
| EP | 2696841 B1 | 10/2018 |
| EP | 3122325 B1 | 10/2018 |
| EP | 2677999 B1 | 12/2018 |
| ES | 2236040 T3 | 7/2005 |
| ES | 2222818 B1 | 3/2007 |
| ES | 2542529 T3 | 8/2015 |
| FR | 1464035 A | 7/1966 |
| FR | 2366841 B1 | 2/1980 |
| FR | 2555443 A1 | 5/1985 |
| FR | 2586693 A1 | 3/1987 |
| FR | 2832062 B1 | 2/2004 |
| FR | 2845596 A1 | 4/2004 |
| FR | 2845284 B1 | 12/2004 |
| FR | 2883170 A1 | 9/2006 |
| FR | 2883171 B1 | 5/2007 |
| FR | 2938188 A1 | 5/2010 |
| FR | 2975295 A1 | 11/2012 |
| FR | 2986429 A1 | 8/2013 |
| FR | 2989891 A1 | 11/2013 |
| GB | 2050829 B | 10/1983 |
| GB | 2270259 A | 3/1994 |
| GB | 2472379 A | 2/2011 |
| JP | 1041602 B2 | 9/1989 |
| JP | 2037206 B2 | 8/1990 |
| JP | 8092061 A | 4/1996 |
| JP | H11137212 A | 5/1999 |
| JP | 2954640 B2 | 9/1999 |
| JP | H11240827 A | 9/1999 |
| JP | 2000072616 A | 3/2000 |
| JP | 2000109421 A | 4/2000 |
| JP | 2000119155 A | 4/2000 |
| JP | 2000212061 A | 8/2000 |
| JP | 2001064150 A | 3/2001 |
| JP | 2001089316 A | 4/2001 |
| JP | 2001107078 A | 4/2001 |
| JP | 2001261570 A | 9/2001 |
| JP | 2002504504 A | 2/2002 |
| JP | 2002080335 A | 3/2002 |
| JP | 2002145723 A | 5/2002 |
| JP | 2003095842 A | 4/2003 |
| JP | 2003261437 A | 9/2003 |
| JP | 2004041010 A | 2/2004 |
| JP | 3519269 B2 | 4/2004 |
| JP | 2004123871 A | 4/2004 |
| JP | 2004137176 A | 5/2004 |
| JP | 2004161655 A | 6/2004 |
| JP | 2004210699 A | 7/2004 |
| JP | 2004210700 A | 7/2004 |
| JP | 2004217616 A | 8/2004 |
| JP | 3615759 B2 | 11/2004 |
| JP | 3643038 B2 | 2/2005 |
| JP | 2005035910 A | 2/2005 |
| JP | 2005041861 A | 2/2005 |
| JP | 2005139139 A | 6/2005 |
| JP | 2005162741 A | 6/2005 |
| JP | 2005232092 A | 9/2005 |
| JP | 2005281133 A | 10/2005 |
| JP | 3739100 B2 | 11/2005 |
| JP | 2005306751 A | 11/2005 |
| JP | 2005320260 A | 11/2005 |
| JP | 3747141 B2 | 12/2005 |
| JP | 2006028133 A | 2/2006 |
| JP | 2006083164 A | 3/2006 |

(56) References Cited

FOREIGN PATENT DOCUMENTS

| | | |
|---|---|---|
| JP | 2006143777 A | 6/2006 |
| JP | 3863675 B2 | 10/2006 |
| JP | 2007106697 A | 4/2007 |
| JP | 2007145716 A | 6/2007 |
| JP | 2007297559 A | 11/2007 |
| JP | 4072296 B2 | 1/2008 |
| JP | 2008143838 A | 6/2008 |
| JP | 2008231010 A | 10/2008 |
| JP | 2009024075 A | 2/2009 |
| JP | 4399332 B2 | 10/2009 |
| JP | 2009269919 A | 11/2009 |
| JP | 4589050 B2 | 9/2010 |
| JP | 2010202595 A | 9/2010 |
| JP | 2010533143 A | 10/2010 |
| JP | 4759912 B2 | 6/2011 |
| JP | 2011213676 A | 10/2011 |
| JP | 2011236176 A | 11/2011 |
| JP | 4931356 B2 | 2/2012 |
| JP | 2012097030 A | 5/2012 |
| JP | 5203623 B2 | 2/2013 |
| JP | 2013053147 A | 3/2013 |
| JP | 2013103892 A | 5/2013 |
| JP | 2013116884 A | 6/2013 |
| JP | 2013121955 A | 6/2013 |
| JP | 2013173730 A | 9/2013 |
| JP | 2013194030 A | 9/2013 |
| JP | 5427422 B2 | 12/2013 |
| JP | 2014001155 A | 1/2014 |
| JP | 2014051670 A | 3/2014 |
| JP | 2014062077 A | 4/2014 |
| JP | 2014080374 A | 5/2014 |
| JP | 2014111579 A | 6/2014 |
| JP | 2015500269 A | 1/2015 |
| JP | 2015147752 A | 8/2015 |
| JP | 2015178485 A | 10/2015 |
| JP | 5857104 B2 | 12/2015 |
| JP | 2016003199 A | 1/2016 |
| JP | 2016027037 A | 2/2016 |
| JP | 2016504377 A | 2/2016 |
| JP | 2016044171 A | 4/2016 |
| JP | 2016069306 A | 5/2016 |
| JP | 2016077836 A | 5/2016 |
| JP | 2016098199 A | 5/2016 |
| JP | 6005863 B2 | 9/2016 |
| JP | 2016183152 A | 10/2016 |
| JP | 2016532654 A | 10/2016 |
| JP | 6017953 B2 | 11/2016 |
| JP | 2016536305 A | 11/2016 |
| JP | 2017501225 A | 1/2017 |
| JP | 6183849 B2 | 8/2017 |
| JP | 6184825 B2 | 8/2017 |
| JP | 2017529368 A | 10/2017 |
| JP | 2017210408 A | 11/2017 |
| JP | 2018505130 A | 2/2018 |
| JP | 6362243 B2 | 7/2018 |
| JP | 2018168102 A | 11/2018 |
| KR | 20000024485 A | 5/2000 |
| KR | 20050006622 A | 1/2005 |
| KR | 20070014412 A | 2/2007 |
| KR | 20080082802 A | 9/2008 |
| KR | 20110007751 A | 1/2011 |
| KR | 20120087600 A | 8/2012 |
| KR | 20130088224 A | 8/2013 |
| KR | 20140001686 A | 1/2014 |
| KR | 20140055689 A | 5/2014 |
| KR | 1405615 B1 | 6/2014 |
| KR | 20140093349 A | 7/2014 |
| KR | 20140132243 A | 11/2014 |
| KR | 20150066811 A | 6/2015 |
| KR | 20160002093 A | 1/2016 |
| KR | 20160096548 A | 8/2016 |
| KR | 20160101371 A | 8/2016 |
| KR | 20160108971 A | 9/2016 |
| KR | 20160109869 A | 9/2016 |
| KR | 20170115956 A | 10/2017 |
| KR | 20180008071 A | 1/2018 |
| KR | 20180020664 A | 2/2018 |
| KR | 20180036232 A | 4/2018 |
| KR | 20180060701 A | 6/2018 |
| KR | 20190001136 A | 1/2019 |
| RU | 2400213 C2 | 9/2010 |
| TW | 201244748 A | 11/2012 |
| WO | 8806888 A1 | 9/1988 |
| WO | 9217159 A3 | 1/1993 |
| WO | 9307856 A1 | 4/1993 |
| WO | 9416710 A1 | 8/1994 |
| WO | 9524179 A1 | 9/1995 |
| WO | 9603970 A1 | 2/1996 |
| WO | 9720540 A1 | 6/1997 |
| WO | 9720542 A1 | 6/1997 |
| WO | 9823256 A1 | 6/1998 |
| WO | 9856343 A1 | 12/1998 |
| WO | 9920229 A1 | 4/1999 |
| WO | 9947141 A1 | 9/1999 |
| WO | 9943296 A3 | 11/1999 |
| WO | 9960995 A1 | 12/1999 |
| WO | 0024921 A1 | 5/2000 |
| WO | 0071093 A1 | 11/2000 |
| WO | 0170187 A1 | 9/2001 |
| WO | 0170188 A1 | 9/2001 |
| WO | 0181635 A1 | 11/2001 |
| WO | 0207685 A2 | 1/2002 |
| WO | 0207700 A2 | 1/2002 |
| WO | 0219984 A3 | 8/2002 |
| WO | 03022234 A1 | 3/2003 |
| WO | 2004024115 A1 | 3/2004 |
| WO | 2005004829 A1 | 1/2005 |
| WO | 2005004833 A1 | 1/2005 |
| WO | 2004100862 A3 | 2/2005 |
| WO | 2005034969 A1 | 4/2005 |
| WO | 2005044214 A1 | 5/2005 |
| WO | 2005049782 A1 | 6/2005 |
| WO | 2006040048 A1 | 4/2006 |
| WO | 2006081071 A1 | 8/2006 |
| WO | 2006127987 A2 | 11/2006 |
| WO | 2007002831 A2 | 1/2007 |
| WO | 2007101493 A1 | 9/2007 |
| WO | 200800534 A1 | 1/2008 |
| WO | 2008003779 A1 | 1/2008 |
| WO | 2008016298 A1 | 2/2008 |
| WO | 2007067735 A3 | 3/2008 |
| WO | 2008112964 A1 | 9/2008 |
| WO | 2009099419 A3 | 5/2010 |
| WO | 2009150408 A3 | 5/2010 |
| WO | 2010051852 A1 | 5/2010 |
| WO | 2010058272 A3 | 7/2010 |
| WO | 2011030123 A2 | 3/2011 |
| WO | 2011033858 A1 | 3/2011 |
| WO | 2011004175 A3 | 4/2011 |
| WO | 2011052224 A1 | 5/2011 |
| WO | 2011074143 A1 | 6/2011 |
| WO | 2012172199 A1 | 12/2012 |
| WO | 2013010032 A1 | 1/2013 |
| WO | 2013088371 A2 | 6/2013 |
| WO | 2011139492 A3 | 7/2013 |
| WO | 2013124820 A1 | 8/2013 |
| WO | 2011038022 A3 | 9/2013 |
| WO | 2013143776 A2 | 10/2013 |
| WO | 2014090513 A1 | 6/2014 |
| WO | 2014131514 A1 | 9/2014 |
| WO | 2014132060 A1 | 9/2014 |
| WO | 2014190128 A1 | 11/2014 |
| WO | 2015007567 A1 | 1/2015 |
| WO | 2015030702 A2 | 3/2015 |
| WO | 2015061512 A1 | 4/2015 |
| WO | 2015117757 A1 | 8/2015 |
| WO | 2015186114 A1 | 12/2015 |
| WO | 2016006821 A1 | 1/2016 |
| WO | 2016034519 A1 | 3/2016 |
| WO | 2015174772 A9 | 6/2016 |
| WO | 2016097965 A1 | 6/2016 |
| WO | 2016100634 A2 | 6/2016 |
| WO | 2016142551 A1 | 9/2016 |
| WO | 2016171464 A1 | 10/2016 |

(56) References Cited

FOREIGN PATENT DOCUMENTS

| WO | 2016188691 | A1 | 12/2016 |
| WO | 2017026405 | A1 | 2/2017 |
| WO | 2017093788 | A1 | 6/2017 |
| WO | 2017123512 | A1 | 7/2017 |
| WO | 2017174756 | A1 | 10/2017 |
| WO | 2017191382 | A1 | 11/2017 |
| WO | 2017194268 | A1 | 11/2017 |
| WO | 2017194292 | A1 | 11/2017 |
| WO | 2017200979 | A1 | 11/2017 |
| WO | 2018062922 | A1 | 4/2018 |
| WO | 2018071640 | A1 | 4/2018 |
| WO | 2018112586 | A1 | 6/2018 |
| WO | 2018134714 | A1 | 7/2018 |
| WO | 2018160509 | A1 | 9/2018 |
| WO | 2018189194 | A1 | 10/2018 |
| WO | 2018191296 | A1 | 10/2018 |
| WO | 2018206962 | A1 | 11/2018 |
| WO | 2019245011 | A1 | 12/2019 |

OTHER PUBLICATIONS

Amico et al., "Effects of Adalimumab, Etanercept and Ustekinumab on the Expression of Psoriasin (S100A7) in Psoriatic Skin", Journal Of Dermatological Science, vol. 80, Issue 1, Oct. 2015, 7 pages.
"Breakout Star Oil-Free Acne Moisturizer", ID#7460333, Tula Life, USA, Mintel GNPD [online], Mar. 2020, Retrieved from Internet: URL:https://portal.mintel.com.
All Office Actions, U.S. Appl. No. 15/402,332.
All Office Actions, U.S. Appl. No. 16/010,944.
All Office Actions, U.S. Appl. No. 16/015,502.
All Office Actions, U.S. Appl. No. 16/460,308.
All Office Actions, U.S. Appl. No. 16/860,837.
All Office Actions, U.S. Appl. No. 16/891,491.
All Office Actions, U.S. Appl. No. 17/215,988.
All Office Actions, U.S. Appl. No. 17/335,718.
Bissett et al., "Topical niacinamide reduces yellowing, wrinkling, red blotchiness, and hyperpigmented spots in aging facial skin", International Journal of Cosmetic Science, 2004, vol. 26, pp. 231-238.
Draelos et al., "Niacinamide-containing facial moisturizer improves skin barrier and benefits subjects with rosacea", Cutis, vol. 76, Aug. 2005, pp. 135-141.
Ebanks et al., "Mechanisms Regulating Skin Pigmentation: The Rise and Fall of Complexion Coloration", International Journal of Molecular Sciences, vol. 10, No. 9, Sep. 2009, pp. 4066-4087.
Eisele et al., The partial compositional characteristics of apple juice from 175 apple varieties, Journal of Food Composition and Analysis, vol. 18, No. 2-3, Mar. 1, 2005, pp. 213-221.
Ekman, et al., Overexpression of Psoriasin (S100A7) Contributes to Dysregulated Differentiation in Psoriasis, Acta Derm Venereol, Apr. 6, 2017, 97(4); 441-448.
Ferraz et al., "Kinetic α-Deuterium Isotope Effects for Enzymatic and Nonenzymatic Hydrolysis of Nicotinamide-β-Riboside", Archives of Biochemistry and Biophysics, vol. 191, No. 2, Dec. 1978, pp. 431-436.
Gillbro, et al., The use of gene arrays and corresponding connectivity mapping (Cmap) to identify novel anti-ageing ingredients, International Journal of Cosmetic Science, 2015, 37 (Suppl. 1), 9-14.
Glaser, et al., The Antimicrobial Protein Psoriasin (S100A7) Is Upregulated in Atopic Dermatitis and after Experimental Skin Barrier Disruption, Journal of Investigative Dermatology (2009), 129(3), 641-649; published online Aug. 28, 2008.
Hakozaki et al., "The effect of niacinamide on reducing cutaneous pigmentation and suppression of melanosome transfer", British Journal of Dermatology, vol. 147. No. 1, Jul. 1, 2002, pp. 20-31.
Khalifah et al., Kinetics of Nonenzymatic Glycation of Ribonuclease A Leading to Advanced Glycation End Products. Paradoxical Inhibition by Ribose Leads to Facile Isolation of Protein Intermediate for Rapid Post-Amadori Studies, Biochemistry, vol. 35, No. 15, Apr. 16, 1996, pp. 4645-4654.
Kimball et al., "Reduction in the appearance of facial hyperpigmentation after use of moisturizers with a combination of topical niacinamide and N-acetyl glucosamine: results of a randomized, double-blind, vehicle-controlled trial", British Journal of Dermatology 2010, vol. 162, No. 2, pp. 435-441.
Oppenheimer, Norman J., "NAD hydrolysis: Chemical and enzymaticmechanisms", Molecular and Cellular Biochemistry, vol. 138, 1994, pp. 245-251.
Seppic, "Sepimax (TM) Zen", Datasheet, 2015. 4 Pages.
Sinthupoom et al., Nicotinic acid and derivatives as multifunctional pharmacophores for medical applications, European Food Research and Technology, vol. 240, No. 1, Oct. 29, 2014, pp. 1-17.
Soma et al., "Moisturizing effects of topical nicotinamide on atopic dry skin", International Journal of Dermatology, vol. 44, No. 3, Mar. 2005, pp. 197-202.
Stillman, Alfred E., "Jaundice", Clinical Methods: The History, Physical, and Laboratory Examinations, Edition 3. 1990. Chapter 87, Available from: https://www.ncbi.nlm.nih.gov/books/NBK413/, pp. 448-456.
Superdrug B. Confident Night Serum, https://www.skincarisma.com/products/b/confident-night-serum/ingredient_list#info-section.
Trojahn et al., Characterizing Facial Skin Ageing in Humans : Disentangling Extrinsic from Intrinsic Biological Phenomena, BioMed Research International, vol. 2015, Article ID 318586, 9 pages, http://dx.doi.org/10.1155/2015/318586, Jan. 14, 2015.
U.S. Appl. No. 17/215,988, filed Mar. 29, 2021, to first inventor Lu (NMN) Zhang.
U.S. Appl. No. 17/335,718, filed Jun. 1, 2021, to first inventor Lu Zhang.
Wohlrab, et al., "Niacinamide—Mechanisms of Action and Its Topical Use in Dermatology", Skin Pharmacology and Physiology 2014; vol. 27, pp. 311-315.
www.gnpd.com Record ID: 2347755, "Dark Circle Correcting Eye Swirl", Apr. 2014, 03 pages.
www.gnpd.com Record ID: 3497875, Tria Age-Defying Skincare Nourishing Eye Renewal Cream, Nov. 2015, 05 pages.
www.gnpd.com Record ID: 3708793, Anti-Wrinkle Face Cream, Neogen Agecure, Mar. 2016, 05 Pages.
Zackheim H.S., Treatment of Psoriasis With 6-Aminonicotinamide. Arch Dermatol. 1975;111(7):880-882. doi: 10.1001/archderm.1975.01630190070007.
All Office Actions; U.S. Appl. No. 17/688,126, filed Mar. 7, 2022.
Chen Jian, Principles of Food Chemistry, South China University of Technology Press, dated Feb. 28, 2015, pp. 145-146.
U.S. Appl. No. 17/688,126, filed Mar. 7, 2022, to first inventor Tomohiro (NMN) Hakozaki et. al.
Mintel, Sym-Micro Essence, Retrieved from Internet: http://www.gnpd.com, May 2020, 9 pages.

METHOD OF IMPROVING PENETRATION OF A VITAMIN B3 COMPOUND INTO SKIN

FIELD

The present invention relates generally to a method of improving the penetration of a vitamin $B_3$ compound into skin. More specifically, the present invention relates to a skin care regimen in which a low-pH skin care composition containing a vitamin $B_3$ compound is applied to the skin, followed by the application of another skin care composition containing a higher amount of the vitamin $B_3$ compound.

BACKGROUND

Skin is the first line of defense against environmental insults that would otherwise damage sensitive underlying tissue and organs. For example, skin maintains a relatively water-impermeable barrier between an organism and its environment to prevent dehydration. Additionally, skin plays a key role in a person's physical appearance. Generally, most people desire to have younger, healthy looking skin. And to some of these people, the tell-tale signs of skin aging such as thinning skin, wrinkles, and age spots are an undesirable reminder of the disappearance of youth.

Both intrinsic and extrinsic factors can lead to a decline in skin appearance and function. For example, as skin ages naturally, there is typically a reduction in the cells and blood vessels that supply the skin and a flattening of the dermal-epidermal junction, which leads to thinning and general degradation of the skin's barrier function. Additionally, lifestyle choices and exposure to the environment (e.g., ultraviolet radiation, pollution, cigarette smoke, smog, wind, heat, low humidity, harsh surfactants, abrasives) may lead to the premature appearance of age spots and uneven skin tone. As a result, treating the signs of aging in skin has become a booming business in youth-conscious societies. Treatments range from cosmetic creams and moisturizers to various forms of cosmetic surgery.

Numerous agents, both natural and synthetic, are known for use in skin care compositions marketed to treat various skin conditions, especially those associated with aging. One example of a class of well-known skin care agents are vitamin $B_3$ compounds such as niacinamide, which have been used in the cosmetics industry to provide a variety of skin health benefits. For example, U.S. Pat. No. 5,833,998 discloses the use of niacinamide for regulating the oily/shiny appearance on skin, and U.S. Pat. No. 5,968,528 discloses the use of niacinamide for regulating the signs of skin aging. More recent studies have suggested that low-pH compositions containing niacinamide may improve efficacy, for example, as described in U.S. Pat. No. 9,833,398 and U.S. Publication No. 2020/0009123. However, low pH niacinamide compositions can sometimes suffer from stability problems due to their ability to ionize and complex with other ingredients in the composition. Thus, formulating with niacinamide at low pH may limit formulation flexibility. Additionally, it is believed, without being limited by theory, that ionized forms of niacinamide can inhibit penetration through the skin barrier, which is comprised of highly keratinized corneocytes in a lipid matrix.

Accordingly, it would be desirable to provide a method of improving skin penetration of a vitamin $B_3$ compound. It would also be desirable to improve skin penetration of a stable vitamin $B_3$ compound from a low-pH composition.

SUMMARY

A method of improving skin penetration of a vitamin $B_3$ compound, comprising: identifying a target portion of skin where a skin health or appearance benefit is desired; applying a low-pH skin care composition to the target portion of skin, wherein the low-pH skin care composition comprises a first concentration of a vitamin $B_3$ compound; and thereafter applying a second skin care composition to the target portion of skin, wherein the second skin care composition comprises a second concentration of the vitamin $B_3$ compound, and the second concentration is higher than the first concentration.

DETAILED DESCRIPTION

Figure 1:
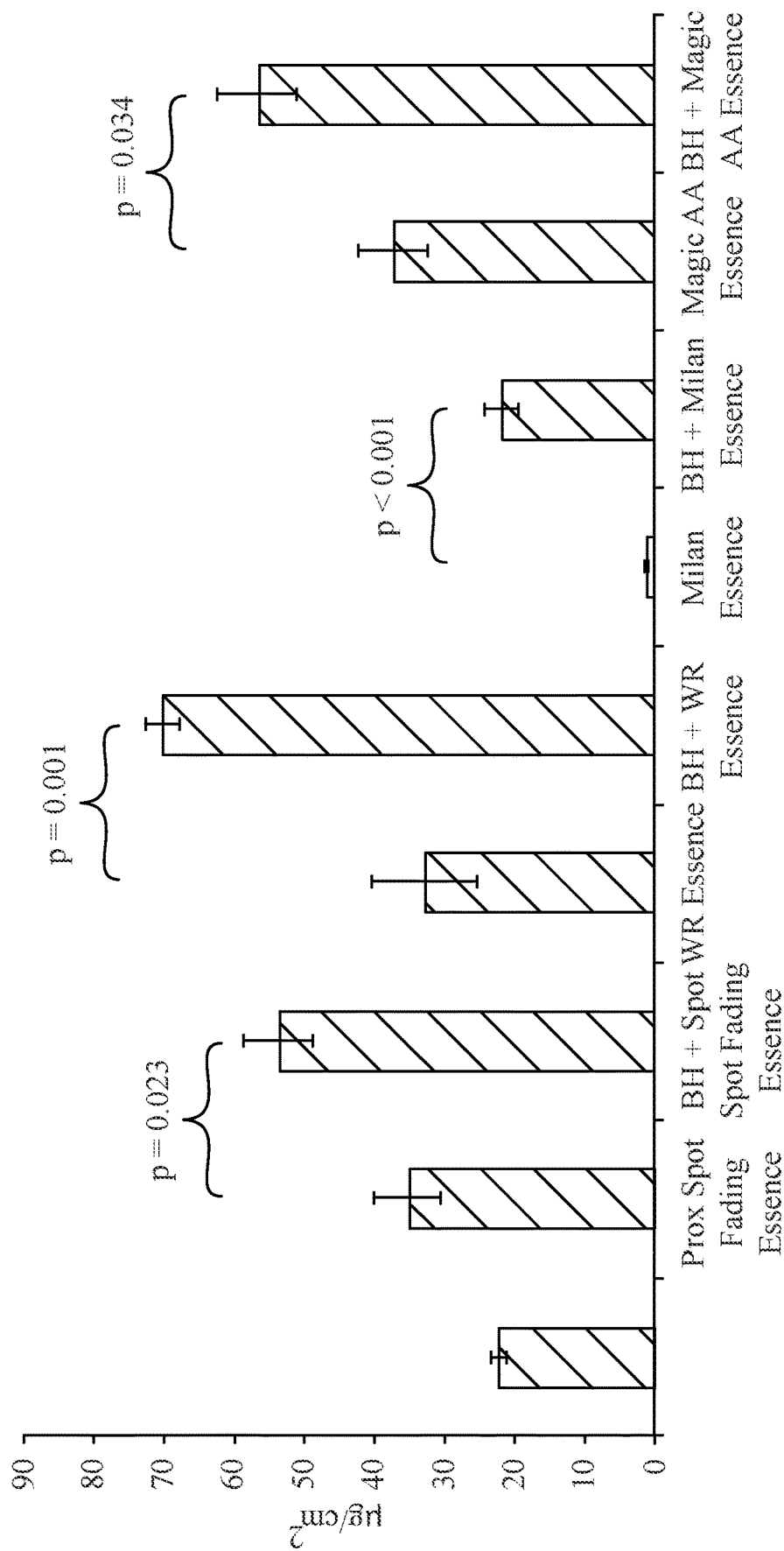
FIG. 1 illustrates results of the skin penetration assay.

The ability of vitamin $B_3$ compounds to provide a skin health and/or appearance benefit is well known. However, in order to provide the desired benefit, a vitamin $B_3$ compound must be able to penetrate the skin, which is governed generally by Fick's law of diffusion. Fick's law of diffusion provides that the flux of a vitamin $B_3$ compound through the skin is directly proportional to the concentration differential of the vitamin $B_3$ compound. Fick's law can be applied using the following equation:

$J=KD(\Delta C/h)$, where:

J is the material flux;
K is the partition coefficient from formulation;
D is the diffusion coefficient into skin;
$\Delta C$ is the concentration differential; and
H is the distance travelled (e.g., stratum corneum thickness).

Thus, when a combination of compositions comprising different concentrations of vitamin $B_3$ compound are applied to the skin, for example, as a regimen (i.e., sequentially), the lower concentration composition effectively dilutes the higher concentration composition, which should result in an overall lower flux of niacinamide through the skin, as compared to the higher concentration composition alone. However, it now been surprisingly discovered that by first applying a low-pH composition containing a vitamin $B_3$ compound to the skin followed by second skin care composition containing a higher concentration of niacinamide, the flux of the vitamin $B_3$ compound through the skin is much higher than expected, even exceeding the individual flux of the higher concentration composition in some instances. This finding is particularly unexpected, since the low pH formula facilitates greater ionization of vitamin $B_3$, thus reducing its expected permeability. This synergistic increase in the flux of the vitamin $B_3$ through the skin provides a number of potential benefits such as, for example, formulation flexibility and improved efficacy of a skin care composition and/or regimen.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to induce a positive benefit to keratinous tissue over the course of a treatment period. The positive benefit may be a health, an appearance, and/or a feel benefit, including, independently or in combination, the benefits disclosed herein. The effective amount of a compound or composition may be demonstrated using ex vivo and/or in vitro methods.

"Improve the appearance of" means providing a measurable, desirable change or benefit in skin appearance, which may be quantified, for example, by a decrease in redness, inflammation, and/or plaque scales.

"Low pH" means a pH of less than 5.0 (e.g., 1.5 to 4.9, 2.0 to 4.5, 2.5 to 4.0, or 3.5 to 4.0). A suitable method of determining the pH of a composition is described in more detail below.

"Neutral pH" means a pH of between 5.0 and 8.0.

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Synergy," and variations thereof, mean that the effect provided by a combination of two or more compounds, materials, and/or compositions is more than the expected effect for each of them individually. For example, synergy can be demonstrated by a more than expected skin penetration of a vitamin $B_3$ compound from two composition with different concentrations of the vitamin $B_3$ compound.

"Treatment period," as used herein, means the length of time and/or frequency that a material or composition is applied to a target skin surface.

"Vehicle control" means a negative control that is identical to the test composition except that it does include the particular active(s) of interest (e.g., does not contain a vitamin $B_3$ compound).

Regimen

The method herein comprises sequentially applying at least two skin care compositions to a target portion of skin where treatment is desired. The first skin care composition is a low-pH composition that contains niacinamide and, optionally, other ingredients commonly used in cosmetic skin care compositions. The low-pH composition is formulated to provide a skin health or appearance benefit while providing good sensory properties and a low potential for skin irritation. The second skin care composition is applied after the low-pH composition (e.g., between 30 seconds and 5 minutes later). The second skin care composition contains a higher concentration of vitamin $B_3$ compound than the low-pH composition and, optionally, includes other optional ingredients commonly used in skin care compositions. The first and second compositions are described in more detail below. While the present regimen is described in the context of applying two skin care compositions in sequence, it is to be appreciated that the method contemplates applying any number of skin care compositions in sequence, after application of the low-pH composition.

The present method involves identifying a target portion of skin on a person in need of treatment or where treatment is desired (e.g., portions of skin that exhibits sings of skin aging such as fine lines, wrinkles, dryness, uneven skin tone, hyperpigmented spots) and applying an effective amount of the first and second skin care compositions to the target portion of skin over the course of a treatment period. The effective amount of a composition may vary based on the skin benefit desired by the user, the size of the treatment area, and/or the concentration of skin care active (e.g., vitamin $B_3$ compound) in the composition. In some instances, the effective amount may range from 0.1 g to 5 g (e.g., 0.2 g to 4 g, 0.3 g to 2 g, or even 0.5 g to 1 g). The target portion of skin may be on a facial skin surface such as the forehead, perioral, chin, periorbital, nose, and/or cheek) or another part of the body (e.g., hands, arms, legs, back, chest). In some instances, a target portion of skin may be selected that does not currently exhibit signs of skin aging, such as hyperpigmented spots or uneven skin tone, but is an area of skin that commonly exhibits such features with age. In these instances, the low-pH composition may be used to help prevent the occurrence of such undesirable skin features.

The composition may be applied locally to the target portion of skin in need of treatment and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions may improve the appearance and/or function of skin, for example, by improving skin texture. Improvements in skin texture can be provided, for example, by decreasing pore size, reducing skin roughness, reducing the presence and/or size of wrinkles, combinations of these and the like.

The treatment period is ideally of sufficient time for the low-pH composition to improve the appearance and/or function of the target portion of skin. The treatment period typically lasts for at least 1 week (e.g., about 2 weeks, 4 weeks, 8 weeks, or even 12 weeks). In some instances, the treatment period may extend over multiple months (i.e., 3-12 months). In some instances, the composition is applied most days of the week (e.g., at least 4, 5 or 6 days a week), at least once a day or even twice a day during a treatment period of at least 2 weeks, 4 weeks, 8 weeks, or 12 weeks.

The step of applying the composition herein may be accomplished by localized application. In reference to application of the composition, the terms "localized", "local", or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Low-pH Composition

The skin care composition herein is a low-pH composition intended for topical application to human skin for improving skin appearance and/or function. In some instances, the present low-pH composition may be used for cosmetic (i.e., non-therapeutic) treatment of a variety of skin conditions such as hyperpigmentation (e.g., age spots), uneven skin tone, sallow looking skin, skin dullness, erythema, dry skin, sebum secretion, rough texture, fine line, wrinkles, keratosis, combinations of these and the like. In some instances, the low-pH composition may be particularly suitable for improving the appearance of hyperpigmented spots, uneven skin tone, and/or sallow looking skin.

The low-pH compositions include an effective amount of a vitamin $B_3$ compound, a polymer thickener that can tolerate low-pH environments, a salt/acid pH buffering system (e.g., lactic acid/sodium lactate and/or glycolic acid/ sodium gluconate) and, optionally, a low molecular weight silicone oil. The composition may optionally include a silicone emulsifier as well as other ingredients commonly found in topical skin care compositions. It is believed, without being limited by theory, that this combination of ingredients provides an efficacious skin care composition that has good feel properties and is gentle on skin.

The low-pH compositions herein may be made by mixing the ingredients with a dermatologically acceptable carrier using conventional methods known to those skilled in the art. The low-pH compositions may be provided in various product forms such as solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), and the like. The composition form may follow from the particular dermatologically acceptable carrier chosen. In some instances, the low-pH composition herein may be in the form of an essence. An essence is a form of topical skin care composition in a relatively concentrated formula that typically has a lower viscosity than conventional cream or lotion-type skin care compositions. In some instances, an essence may be provided in the form of a low-viscosity fluid that is marketed to specifically target a particular skin condition and/or be used in the first step of a skin care regimen. An essence product herein may have a dynamic viscosity of 1 centipoise (cP) to 30,000 cP at 25° C. (e.g., 50 cP to 10,000 cP or 100 cP to 7,500 cP, 200 cP to 5,000 cP, or 300 cP to 2,500 cP). The viscosity of a low-pH composition herein is determined according to the Rheology Method provided in the Methods section below.

It has been found that at least some consumers desire a skin care essence that has a certain balance of transparency and opacity. If the essence is too transparent, it looks too much like water and consumers may be skeptical of the efficacy of the product. But if the essence is too opaque, consumers may think that product will not provide the light, clean feel that is expected from an essence. Thus, the low pH essence product herein has an opacity of between 15 and 75 (e.g., between 20 and 60 or between 25 and 50), according to the Opacity Test, which is described in more detail below. In some instances, it may be desirable to limit the amount of hydrocarbon oils such as fatty alcohols and mineral oils present in the low pH essence, as these ingredients can undesirably increase the opacity of the essence. Accordingly, it may be desirable to provide a low pH essence that is free or substantially free of hydrocarbon oils (e.g., less than 3%, 2%, 1%, 0.5%, or even 0%). Some nonlimiting examples of suitable low-pH compositions are described in co-pending U.S. Ser. No. 16/891,491.

Vitamin $B_3$ Compound

The present composition includes a safe and effective amount of a vitamin $B_3$ compound for regulating a variety of skin condition, for example, as described in U.S. Pat. No. 5,939,082. The compositions herein may contain 0.1% to 10%, by weight, of the vitamin $B_3$ compound, based on the weight or volume of the composition (e.g., 0.5% to 5% or 1% to 4%).

As used herein, "vitamin $B_3$ compound" means a compound having the formula:

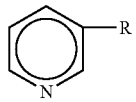

Where:
R is $CONH_2$ (i.e., niacinamide), COOH (i.e., nicotinic acid) or $CH_2OH$ (i.e., nicotinyl alcohol); derivatives thereof; and salts of any of the foregoing. Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide. In some instances, vitamin $B_3$ compounds such as niacinamide may have improved efficacy at lower pH, for example, as described in U.S. Publication No. 2020/0009123.

In some instances, it may be desirable for the ring nitrogen of the vitamin $B_3$ compound to be "uncomplexed" (e.g., chemically unbound and/or unhindered) in the composition and/or prior to application to a target skin surface. For example, the compositions herein may be free of or substantially free of (i.e., less than 3%, 2%, 1% or even less than 0.5%) a salt or complex of a vitamin $B_3$ compound. Exemplary approaches to minimizing or preventing the formation of undesirable salts and/or complexes include omission of materials that form substantially irreversible or other undesirable complexes with the vitamin $B_3$ compound in the composition, pH adjustment, ionic strength adjustment, the use of surfactants, and practicing formulation processes wherein the vitamin $B_3$ compound and materials which complex therewith are in different phases.

Low-pH Buffering System

When providing a low-pH composition for topical application to skin, it is important to include a buffering system to help maintain the pH of the composition after it is applied to the skin. On average, human skin pH typically ranges from about 5.0 to 6.0. To maintain this pH, human skin has evolved a natural buffering system that resists changes to pH. Thus, when a low-pH composition is applied to the skin, the skin's natural buffering system will try to adjust the pH of the composition to match the natural pH of the skin. Without the addition of the buffering system, the low-pH composition may not be able to provide the desired skin care benefit.

The low-pH buffering system herein includes an acid buffering agent. A variety of acids are known for use in skin care compositions. For example, alpha hydroxy acids (e.g., citric acid, glycolic acid, malic acid, and lactic acid), beta hydroxy acids (e.g., salicylic acid and propanoic acid), and polyhydroxy acids (e.g., gluconic acid) are commonly used as exfoliants. However, some acids are stronger than others and/or some people may be more sensitive to certain concentrations of acids than others. Both of these factors can increase the risk of skin irritation caused by a low-pH composition containing an acid. Some non-limiting examples of acids that may be suitable for use as an acid buffering agent herein are lactic acid, gluconic acid, lactobionic acid, and/or maltobionic acid. Lactic acid and gluconic acid may be particularly suitable because they tend to be relatively gentle on skin (i.e., less likely to cause skin irritation) compared to other acids. However, lactic acid and gluconic acid are still strong enough to provide the desired low pH in the present composition. In addition, composition containing lactic acid and/or gluconic acid may provide skin benefits may provide additional skin benefits such as improving the skin's natural moisture factor and/or stimulating collagen renewal to help improve visible signs of aging skin. The low-pH compositions herein may include 0.5% to 5% of a suitable acid buffering agent. In some instances, the low-pH composition may include 0.75% to 4%, 1% to 3%, or 1.5% to 2.5% of the acid buffering agent. It is to be appreciated that the acid buffering agent may be added in a form that readily converts to the desired acid. For example, glucono delta lactone and other gluconic acid precursors that readily convert to gluconic acid in the present compositions are considered gluconic acid for purposes of the present invention.

The low-pH buffering system herein includes a suitable salt buffering agent, which may depend on the acid buffering agent selected. For example, it may be desirable to use sodium lactate, when the acid buffering agent is lactic acid and/or sodium gluconate when the acid buffering agent is gluconic acid. Other non-limiting examples of salts that may be suitable for use herein include additional salt buffering agent selected from calcium lactate gluconate, potassium lactate, zinc lactate, and potassium gluconate. The salt buffering agent may be present at any amount suitable to provide the buffering capability for maintaining the desired low pH of the composition upon application to the skin and for at least 1 minute thereafter (e.g., 5, 10, 15, 30, 60 or even 120 minutes or more after application) in order to provide enough time for the active ingredients in the composition to penetrate into the skin. In some instances, the salt buffering agent may be present in the low-pH composition at 0.25% to 4% (e.g., 0.5% to 3%, 0.75% to 2% or 1% to 1.75%). In some instances, the salt buffering agent may be present at a weight ratio of acid to salt of 1:10 to 10:1. It may be desirable to use the L-enantiomer form of the acid and/or salt buffering agents, since that is the form that occurs naturally in the body. Sodium lactate may be particularly suitable for use as a salt buffering agent because it may also act as a humectant to help moisturize the skin. Of course, it is to be appreciated that the present composition may optionally include other pH buffers known for use in skin care compositions.

Thickeners

The low-pH compositions herein include a polymer thickener that can tolerate a low pH, electrolytic environment. That is, the thickener will not lose its ability to thicken or stabilize the composition at low pH in the presence of an acid-salt buffering system, Some conventional neutralized thickeners are known to degrade and/or lose the ability to suitably thicken a composition at lower pH and/or in the presence of an acid-salt buffer (e.g., lactic acid/sodium lactate and gluconic acid/sodium gluconate). For example, some neutralized thickeners degrade in a low pH environment. On the other hand, fatty alcohol thickeners such as cetyl alcohols and stearyl alcohols are generally stable at low pH, but tend to impart an undesirable cloudiness or opacity to the composition when it is in the form of an essence, serum, or the like. It has also been found that certain anionic polymeric thickeners can provide suitable tolerance to low pH environments but cannot tolerate buffer systems due to combination of acid and salt. Thus, in some instances, the low-pH composition described herein may be free or substantially free of neutralized thickeners, fatty alcohol thickeners, and anionic thickeners. The thickener may be present at 0.0001% to 25% (e.g., 0.001% to 20%, 0.01% to 10%, 0.5% to 7%, or 1% or 5%) by weight of the composition.

Other nonlimiting examples of thickeners or water structuring agents that may be used alone or in combination herein include natural or synthetic gums, polysaccharides, carboxylic acid polymers, polyacrylamide polymers, sulfonated polymers, and copolymers of these. Further examples include modified gums, celluloses, and superabsorbent polymers. The term "superabsorbent polymer" is understood to mean a polymer which is capable, in its dry state, of spontaneously absorbing at least 20 times its own weight of aqueous fluid, in particular of water and especially of distilled water. Suitable polysaccharides include alkyl hydroxyalkyl cellulose ethers, such as hydroxypropylmethylcellulose stearoxy ether. This material is sold under the tradename of SANGELOSE 60L and 90L from Daido Chemical Corp. Another suitable polysaccharide includes hydrophobically modified starch, such as Potato modified starch. This material is sold under the tradename of STRUCTURE SOLANACE by Nouryon. Another polymer includes crosslinked polymers, the monomers of which are at least partially composed of acryloyldimethyltaurate monomers, such as, for example sodium polyacryloyldimethyl taurate, sold under the tradename of ARISTOFLEX SILK, from Clariant.

It has now been found that certain anionic polymeric thickeners can provide suitable tolerance to low pH environments and the desired feel and opacity properties to the composition. Thus, a particularly suitable example of an anionic thickener is polyacrylate crosspolymer-6, which is commercially available as SEPIMAX ZEN from Seppic, France.

Tack Reducing Oil

In some instances, an anionic polymeric thickener may impart an undesirable tacky feel when the low-pH composition is applied to a target portion of skin. It has been found that the addition of certain oils (e.g., low molecular weight hydrocarbon or silicone oils) can reduce or prevent this tacky feel. Low molecular weight silicone oils may be particularly desirable as they tend to provide a smooth, velvety feel that consumers prefer over hydrocarbon oils, which can sometimes feel greasy. The molecular weight of a silicone oil depends on the length of its silicone polymer chain(s), which is also directly proportional to the viscosity of the silicone oil. Thus, the low molecular weight silicone oil suitable for use in the present low-pH composition have a kinematic viscosity of 100 cSt or less at 25° C. (e.g., 1 cSt to 90 cSt, 5 cSt to 50 cSt, or even 10 cSt to 30 cSt). Kinematic viscosity is a common method of classifying silicone oils and can be obtained from the supplier of the material. A particularly suitable example of a low molecular weight silicone oil is 5 cSt dimethicone fluid. As used herein, "dimethicone" means a polydimethylsiloxane compound having the formula:

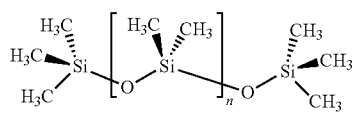

Second Skin Care Composition

The second skin care composition for use in the present regimen is not particularly limited and can include a wide variety of skin care compositions that contain a vitamin $B_3$ compound and are suited for topical application to skin. The second skin care composition may be provided in various product forms that include, but are not limited to, solutions, suspensions, lotions, creams, gels, toners, sticks, pencil, sprays, aerosols, ointments, cleansing liquid washes (rinse-off or leave-on) and solid bars, foams, powders, mousses, shaving creams, wipes, strips, patches, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

Dermatologically Acceptable Carrier

The low-pH and second skin care compositions herein may include a dermatologically acceptable carrier ("carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Nonlimiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsifier

When a composition herein is in the form of an emulsion (e.g., oil-in-water emulsion), it may be desirable to include art emulsifier to stabilize the emulsion (i.e. prevent the emulsion from phase separating). The emulsifier may be present in the composition at 0.01% to 10% (e.g., 0.05% to 5% or 0.1% to 2%). The emulsifiers may be nonionic, anionic or cationic. In some instances, the emulsifier may be a silicone emulsifier. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Some other non-limiting examples of emulsifiers that may be suitable for use herein include ethers of polyglycols and of fatty alcohols, esters of polyglycols and of fatty acids, ethers of polyglycols and of fatty alcohols which are glycosylated, esters of polyglycols and of fatty acids which are glycosylated, ethers of C12-30 alcohols and of glycerol or of polyglycerol, esters of C12-30 fatty acids and of glycerol or of polyglycerol, ethers of oxyalkylene-modified C12-30 alcohols and of glycerol or polyglycerol, ethers of C1-230 fatty alcohols comprising and of sucrose or of glucose, esters of sucrose and of C1230 fatty acids, esters of pentaerythritol and of C12-30 fatty acids, esters of sorbitol and/or of sorbitan and of C12 30 fatty acids, ethers of sorbitol and/or of sorbitan and of alkoxylated sorbitan, ethers of polyglycols and of cholesterol, esters of C12-30 fatty acids and of alkoxylated ethers of sorbitol and/or sorbitan, and combinations thereof. A particularly useful class of emulsifiers is polyethylene glycol ethers of lauryl alcohol such as laureth-1 through laureth-50 (e.g., laureth-4). Still other examples of emulsifiers include ethers of glycerol, polyglycerol, sucrose, glucose, or sorbitol; esters of glycerol, polyglycerol, sucrose, glucose, or sorbitol; and mixtures thereof. Other particularly useful classes of emulsifiers are the alkyl esters of sorbitol and sorbitol anhydrides such as polysorbate 20, polysorbate 21, and polysorbate 40.

Silicone emulsifiers may suitable for use herein. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin-Etsu. A particular suitable emulsifier for use herein is PEG-11 methyl ether dimethicone, which is available from Shin-Etsu as KF-6011. Surprisingly, it was discovered that the PEG-11 methyl ether dimethicone emulsifier further reduced the tacky feel of the anionic polymer thickener, thereby improving the overall feel of the low-pH composition. The emulsifier may be present at an amount of 0.1% to 10% (e.g., 1% to 5%, or 2%-4%).

Other Optional Ingredients

The low-pH and second skin care compositions may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Some non-limiting examples of skin care compositions and additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Methods

Opacity Test Method

This method is used to determine the opacity of a product or material. Results are reported as a percentage, wherein higher the percentage the greater is the opacity of the sample. Prior to measuring opacity, mill the test composition to be tested using an Ultra-turrax T25 (from IKA, Germany) or equivalent with a S 25 N-25 F Dispersing tool (or equivalent) for 1 min at 10,000 rpm taking care not to introduce air into the sample. Prepare the sample by placing a sufficient amount of the composition in a suitable transmittance cell that provides a 2 mm optical path (e.g., CM-A130 rectangular cells from Konica Minolta or equivalent). Measure the opacity of the sample using a suitable spectrophotometer that can deliver tristimulus values CIE XYZ under CIE D65 lighting conditions across the visible spectrum is used for this method (e.g., a CM-3600A Spectrophotometer available from Konica Minolta, or equivalent). Set the spectrophotometer to deliver 1931 CIE defined tristimulus XYZ values with 2° observer and D65 illuminant. Two sets of tristimulus values are necessary to calculate opacity—one with the product's 2 mm sample cell in front of a white background and the other in front of a black background. Acceptable white backgrounds include the white portion of an opacity card (such as Opacity Card Form 2A, Leneta Company, Inc, Mahwah, N.J., USA, or equivalent) and acceptable black backgrounds are the black portion of an opacity card (such as Opacity Card Form 2A, Leneta Company, Inc, Mahwah, N.J., USA, or equivalent). Opacity is determined by calculating the quotient of the Y tristimulus value using the black background divided by the Y tristimulus value using the white background and multiplying by 100%. Opacity is reported to the nearest integer percentage.

Rheology Method

This method provides a way to measure the dynamic viscosity of a composition or material using a BROOKFIELD brand viscometer (e.g., model DV2T or equivalent) and a suitable spindle (e.g., RV4 or equivalent) according to the manufacturer's instructions. It is to be appreciated that the skilled artisan will be able to select the appropriate spindle in accordance with the manufacture's recommendation. After calibrating the viscometer, the spindle is immersed into a sufficient quantity of test sample (e.g., enough to immerse the spindle up to the immersion mark on the spindle shaft). Set the spindle rotation speed to 5 rpm, and then start the viscometer. Allow time for the indicated viscosity reading to stabilize (approximately 10-30 seconds). After the reading stabilizes, take 5 readings at 10 second intervals. Calculate the viscosity as the average of the 5 readings.

EXAMPLES

Example 1—Formulations

Table 1 provides examples of the low-pH skin care compositions described herein. The compositions were prepared using conventional methods of making skin care compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared to optimize stability (physical stability, chemical stability, photostability) and/or delivery of the active materials. This optimization may include adjusting the pH (i.e., to less than 5), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

The pH of the compositions tested in this example are measured with an ORION brand 525A pH meter (or equivalent) equipped with a flat surface electrode/probe (e.g., VWR Cat. 20 No. 89231-584). The probe of the pH meter is immersed directly into a neat sample of the composition.

TABLE 1

| Component | A | B | C | D | E | F | H | I | J* | K | L |
|---|---|---|---|---|---|---|---|---|---|---|---|
| | % | | | | | | | | | | |
| Water | qs | qs | qs | qs | qs | qs | qs | qs | qs | qs | qs |
| Glycerin | 4.5 | 4.5 | 3.0 | 3.0 | 4.5 | 4.5 | 4.5 | 3.0 | 4.5 | 4.5 | 4.5 |
| Dimethicone 5 cSt | 4.0 | 4.0 | 3.0 | 4.0 | 4.0 | 4.0 | 4.0 | 4.0 | — | — | — |
| Dimethicone 50 cSt | — | — | — | — | — | — | — | — | — | 4.0 | — |
| Dimethicone 100 cSt | — | — | — | — | — | — | — | — | — | — | 4.0 |
| Dimethicone and dimethicone/vinyl dimethicone crosspolymer[1] | — | — | — | — | 4 | — | — | — | — | — | — |
| Niacinamide | 0.04 | 2.0 | 2.0 | 2.0 | 2.0 | 2.0 | 2.0 | 2.0 | 2.0 | 2.0 | 2.0 |
| Yeast Extract Hydrolyzed Yeast Protein[2] | — | 3.0 | — | — | — | — | — | — | — | — | — |
| Trifluoroacetyl Tripeptide-2[3] | — | 1.0 | — | — | — | — | — | — | — | — | — |
| Lactic acid | 2.0 | 1.62 | 1.62 | 1.62 | 1.62 | 1.62 | 1.62 | 1.62 | 1.62 | 1.62 | 1.62 |
| Sodium lactate | 1.8 | 0.78 | 0.78 | 0.78 | 0.78 | 0.78 | 0.78 | 0.78 | 0.78 | 0.78 | 0.78 |
| Polyacrylate crosspolymer-6[4] | 1.30 | 1.2 | 1.2 | 1.0 | 1.2 | 1.2 | 1.2 | 1.2 | 1.2 | 1.2 | 1.2 |
| Panthenol | 0.05 | 0.5 | 0.5 | 1.0 | 0.5 | 0.5 | 0.5 | 0.5 | 0.5 | 0.5 | 0.5 |
| Disodium EDTA | 1.0 | 0.1 | — | 0.1 | 0.1 | 0.1 | 0.1 | 0.1 | 0.1 | 0.1 | 0.1 |
| PEG-11 methyl ether dimethicone[5] | 0.1 | 0.1 | 0.1 | — | 0.1 | 0.1 | — | 0.1 | — | 0.1 | 0.1 |
| Laureth-4 | — | — | — | 0.2 | 0.2 | — | — | — | — | — | — |
| Trehalose | 0.1 | 0.1 | 0.1 | 0.1 | 0.1 | 0.1 | 0.1 | 0.1 | 0.1 | 0.1 | 0.1 |
| Xylitol | — | — | — | — | — | — | — | 1.4 | — | — | — |
| Phenoxyethanol | — | — | — | — | — | — | — | 0.25 | — | — | — |
| Sodium Benzoate | 0.05 | 0.05 | 0.05 | 0.05 | 0.05 | 0.05 | 0.05 | 0.05 | 0.05 | 0.05 | 0.05 |
| Fragrance | 0.04 | 0.04 | — | 0.04 | — | — | — | — | — | — | — |
| pH | 3.80 | 3.80 | 3.80 | 3.80 | 3.80 | 3.80 | 3.80 | 3.80 | 3.80 | 3.80 | 3.80 |

TABLE 1-continued

| Component | M | N | O | P | Q | R* | S | T | U | V | W |
|---|---|---|---|---|---|---|---|---|---|---|---|
| | | | | | | % | | | | | |
| Water | qs | qs | qs | qs | qs | qs | qs | qs | qs | qs | qs |
| Glycerin | 4.5 | 4.5 | 5.0 | 4.5 | 4.5 | 4.5 | 4.5 | 4.5 | 5.0 | 5.0 | 5.0 |
| Dimethicone 5 cSt | 4.0 | — | 4.0 | 4.0 | — | — | 4.0 | 4.0 | 4.0 | 4.0 | 4.0 |
| Niacinamide | 2.0 | 2.0 | 2.0 | 2.0 | 2.0 | 2.0 | 2.0 | 2.0 | 5.0 | 5.0 | 5.0 |
| Lactic acid | 1.62 | 1.62 | — | 1.62 | 1.62 | 1.62 | 1.62 | 1.62 | 2.07 | 1.26 | 0.81 |
| Sodium lactate | 0.78 | 0.78 | — | 0.78 | 0.78 | 0.78 | 0.78 | 0.78 | 0.39 | 1.32 | 1.8 |
| Glucono delta lactone | — | — | 3.1 | — | — | — | — | — | — | — | — |
| Sodium gluconate | — | — | 1.8 | — | — | — | — | — | — | — | — |
| Polyacrylate crosspolymer-6 | 1.92 | 1.2 | 1.5 | 1.2 | 1.2 | — | — | — | 1.2 | 1.5 | 1.2 |
| Sodium polyacryloyldimethyl taurate[6] | — | — | — | — | — | 1.2 | 1.2 | 1.2 | — | — | — |
| Panthenol | 0.5 | 0.5 | 0.5 | 0.5 | 0.5 | 0.5 | 0.5 | 0.5 | 0.5 | 0.5 | 0.5 |
| Disodium EDTA | 0.1 | 0.1 | 0.1 | 0.1 | 0.1 | 0.1 | 0.1 | 0.1 | 0.1 | 0.1 | 0.1 |
| PEG-11 methylether dimethicone | 0.1 | — | 0.1 | — | — | — | 0.1 | — | 0.1 | 0.1 | 0.1 |
| Trehalose | 0.1 | 0.1 | — | 0.1 | 0.1 | 0.1 | 0.1 | 0.1 | 0.1 | 0.1 | 0.1 |
| Sodium Benzoate | 0.05 | 0.05 | 0.05 | 0.05 | 0.05 | 0.05 | 0.05 | 0.05 | 0.05 | 0.05 | 0.05 |
| Isopropyl lauroyl sarcosinate[7] | — | 4.0 | — | — | — | — | — | — | — | — | — |
| Isohexadecane | — | — | — | — | 4.0 | — | — | — | — | — | — |
| pH | 3.80 | 3.80 | 3.80 | 3.80 | 3.80 | 3.80 | 3.80 | 3.80 | 3.80 | 4.20 | 4.50 |

| Component | X | Y | Z | AA | AB | AC | AD | AE | AF |
|---|---|---|---|---|---|---|---|---|---|
| | | | | | % | | | | |
| Water | qs | qs | qs | qs | qs | qs | qs | qs | qs |
| Glycerin | 5.0 | 5.0 | 5.0 | 5.0 | 5.0 | 5.0 | 5.0 | 5 | 5 |
| Dimethicone 5 cSt | 4.0 | 4.0 | 4.0 | 4.0 | 4.0 | 4.0 | 4.0 | 4 | 4 |
| Niacinamide | 2.0 | 2.0 | 2.0 | 2.0 | 2.0 | 2.0 | 2.0 | 2 | 2 |
| Lactic acid | 0.9 | 1.26 | — | — | — | — | — | 1.8 | 1.8 |
| Sodium lactate | 1.5 | 1.32 | — | — | — | — | — | — | 0.4 |
| Glucono delta lactone | — | — | 1.36 | 3.1 | — | — | 3.1 | — | — |
| Sodium gluconate | — | — | 1.25 | — | 2.5 | 2.5 | — | — | — |
| Lactobionic acid[8] | — | — | — | — | 5.0 | | — | — | — |
| Maltobionic acid[9] | — | — | — | — | — | 5.0 | — | — | — |
| Calcium lactate gluconate[10] | — | — | — | 1.8 | — | — | — | — | — |
| Potassium gluconate[10] | — | — | — | | — | — | 1.8 | — | — |
| Potassium lactate[10] | — | — | — | — | — | — | — | 1.3 | — |
| Zinc lactate[11] | — | — | — | — | — | — | — | — | 1 |
| Polyacrylate crosspolymer-6 | 1.5 | 1.5 | 1.5 | 1.5 | 1.5 | 1.5 | 1.5 | 1.5 | 1.5 |
| Sodium polyacryloyldimethyl taurate | — | — | — | — | — | — | — | — | — |
| Panthenol | 0.5 | 0.5 | 0.5 | 0.5 | 0.5 | 0.5 | 0.5 | 0.5 | 0.5 |
| Disodium EDTA | 0.1 | 0.1 | 0.1 | 0.1 | 0.1 | 0.1 | 0.1 | 0.1 | 0.1 |
| PEG-11 methylether dimethicone | 0.1 | 0.1 | 0.1 | — | — | — | 0.1 | 0.1 | 0.1 |
| Trehalose | 0.1 | 0.1 | 0.1 | 0.1 | 0.1 | 0.1 | 0.1 | 0.1 | 0.1 |
| Sodium Benzoate | 0.05 | 0.05 | 0.05 | 0.05 | 0.05 | 0.05 | 0.05 | 0.05 | 0.05 |
| pH | 4.20 | 4.50 | 4.11 | 3.77 | 3.95 | 3.95 | 3.80 | 3.80 | 3.70 |

[1]KSG-16 available from Shin-Etsu
[2]CHRONOGEN YST available from Ashland, Inc.
[3]PROGELINE available from Lucas Meyer Cosmetics
[4]SEPIMAX ZEN available from Seppic
[5]KF-6011 available from Shin-Etsu
*Comparative example
[6]ARISTOFLEX SILK available from Clariant
[7]ELDEW SL 205 available from Ajinomoto OmniChem
[8]TEGO RENEWHA LACTO available from Evonik
[9]TEGO RENEWHA MALTO available from Evonik
[10]Available from Jungbunzlauer
[11]PURAMEX Zn from Corbion

Example 2—Improved Skin Penetration of a Vitamin B₃ Compound

This example demonstrates the ability of the present regimen to improve skin penetration of niacinamide. In this example, a low-pH composition (Example I from Table 1) was applied to an ex vivo skin sample followed by application of a second skin care composition. The second skin compositions used in this test included a variety of commercially available skin care compositions from the Procter & Gamble Company. Each of the second skin care compositions contains 5% niacinamide. In the first test (summarized in Table 2A below), skin samples were analyzed to determine the amount of niacinamide that penetrated into the epidermis through the stratum corneum. In the second test (summarized in Table 2B below), the skin samples were analyzed to determine the total amount of niacinamide that penetrated into and/or through the skin sample.

Skin Penetration Method (Franz Cell)

In vitro skin penetration of actives, such as niacinamide, from topically applied formulations can be determined using the Franz diffusion cell assay (Franz, T. J. Percutaneous absorption. On the relevance of in vitro data. J. Invest. Dermatol. 64: 190-195, 1975; Franz, et al. The use of excised human skin to assess the bioequivalence of topical products. Skin Pharmacol. Physiol. 22: 276-286, 2009). The Franz diffusion cell assay is widely used in the skin care industry for assessment of skin penetration and for the dermal absorption safety assessments.

Skin samples are prepared from split-thickness human cadaver skin that is thawed at ambient conditions, cut into appropriately sized sections, and mounted in standard static Franz-type diffusion cells (0.79 cm² surface area) maintained at 37° C. Approximately 5 ml of a receptor solution is placed in the receptor compartments at the bottom of each cell to collect any niacinamide the penetrates through the entire skin sample. The receptor solution is phosphate buffered saline (PBS-pH 7.4) that includes 1% polysorbate-20 and 0.02% sodium azide. The skin samples are equilibrated for two hours. Each treatment group has 6 replicates.

To prepare the test compositions, aliquots of the test compositions are spiked with $^{14}$C-niacinamide with approximately 3 μCi per 300 mg aliquot. The test composition aliquots are mixed and assayed for total radioactivity in triplicate using ULTIMA GOLD brand liquid scintillation cocktail (LSC) (available from PerkinElmer, Boston) or equivalent and a suitable liquid scintillation counter (e.g., TRI-CARB 2500 TR brand liquid scintillation analyzer available from PerkinElmer).

The skin samples are topically dosed with 5 μL of the test composition using a positive displacement pipette. The product is gently spread over the surface of the skin (~0.79 cm²) using a glass rod. When a regimen of two or more products is tested, there is a 3-minute interval between applications. At the end of the test (6 hours after dosing) the receptor solution is collected and the surface of each skin sample is wiped two times with Whatman filter paper soaked with PBS/Tween 20 and once with 70%/30% ethanol/water to remove unabsorbed (residual) product. The epidermis is separated from the dermis by dissection and then the epidermis and dermis sections are dissolved in 0.50-1.25 mL SOLUENE-350 (available from PerkinElmer) at 60° C. overnight. Niacinamide skin penetration is quantitated using liquid scintillation counting as described above. Scintillation counting is performed on the epidermis sample, the dermis sample, and the receptor solution. The amount of epidermal skin penetration is the total amount of fluorescence measured from the epidermis sample (including stratum corneum). Total penetration is the sum of the fluorescence measured from the epidermis sample, the dermis sample, and the receptor compartment. Skin penetration data may be expressed as % of dose and/or ug/cm².

Figure 2:
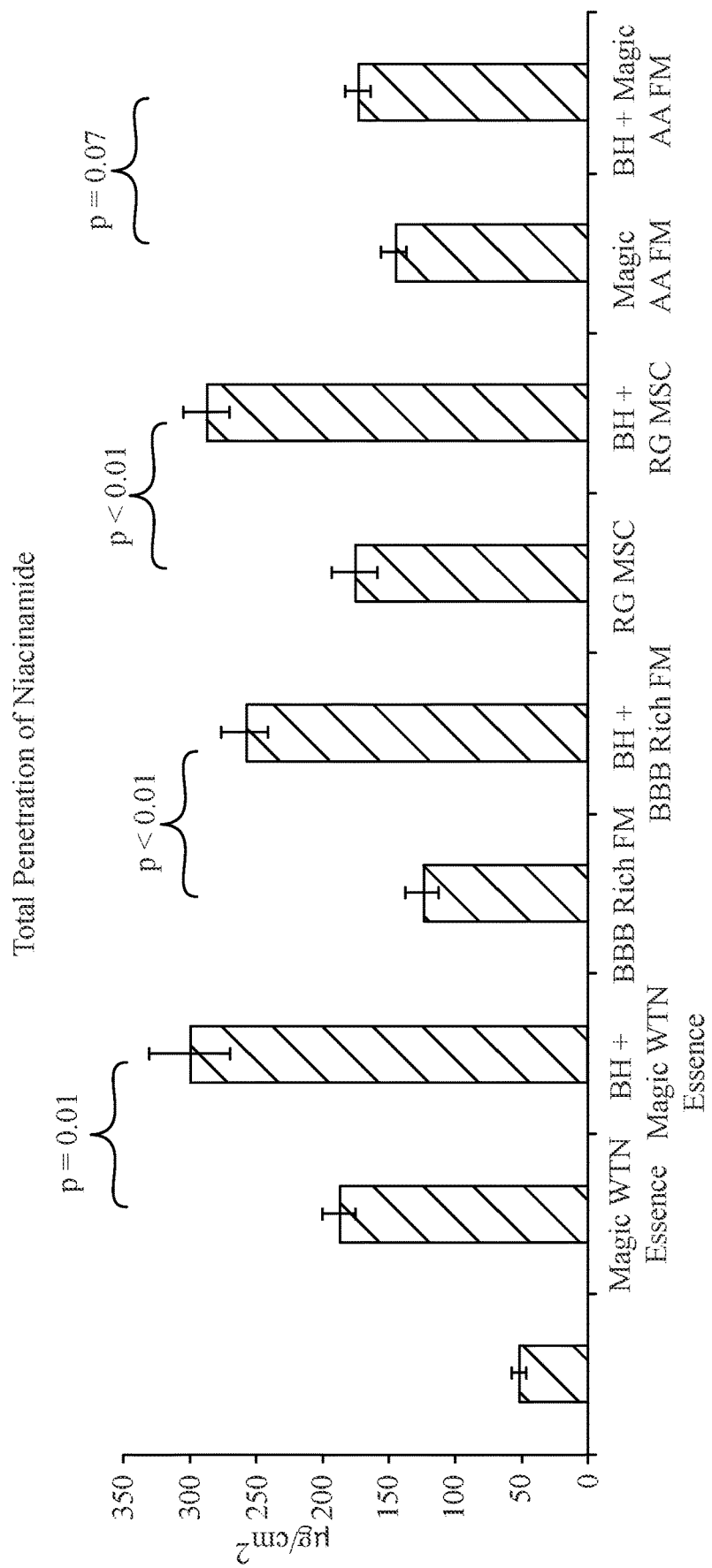
FIG. 2 illustrates results of the skin penetration assay.

The results of the skin penetration tests conducted in this example are summarized in Tables 2A and 2B and illustrated in FIGS. 1 and 2. The expected amount of niacinamide penetration was determined by applying Fick's law of diffusion to the total concentration of niacinamide applied to the target portion of skin. As can be seen in Tables 2A and 2B, the regimen provided an unexpected increase in niacinamide penetration in each case. In some cases, as illustrated in FIGS. 1 and 2, the regimen even provided additive skin penetration results, which would typically only be expected from compositions that have the same concentration of niacinamide, and thus have the same thermodynamic potential for penetration. However, as can be seen with the OLAY REGENERIST CELLSCIENCE Anti-Aging Cream product in Table 2B, not all compositions will provide an unexpected increase in niacinamide skin penetration, even when applied as a regimen with the present low-pH composition.

TABLE 2A

| | Niacinamide penetration into Epidermis (μg/cm²) | | | | | |
|---|---|---|---|---|---|---|
| Second Composition | Measured penetration of low-pH composition | Measured penetration of second composition | Expected penetration of regimen | Measured penetration of regimen | Δ penetration (actual - expected) | Fold change |
| OLAY PROX Spot Fading Essence | 22.41 | 35.34 | 49.48 | 53.76 | 4.28 | 1.52* |
| OLAY White Radiance Essence | 22.41 | 32.94 | 46.12 | 70.27 | 24.15 | 2.13* |
| OLAY PROX Intensive Wrinkle Fading Essence | 22.41 | 1.3 | 1.82 | 22.05 | 20.23 | 16.96* |
| OLAY REGENERIST CELLSCIENCE Anti-Aging Essence | 22.41 | 37.46 | 52.44 | 56.77 | 4.33 | 1.52* |

*p < 0.05 vs. second composition penetration alone

TABLE 2B

Total Niacinamide penetration into Skin (μg/cm$^2$)

| Second Composition | Measured penetration of low-pH composition | Measured penetration of second composition | Expected penetration of regimen | Measured penetration of regimen | Δ penetration (actual - expected) | Fold change |
|---|---|---|---|---|---|---|
| OLAY White Radiance CELLSCIENCE Essence | 52.13 | 187.33 | 262.26 | 300.19 | 37.93 | 1.60* |
| OLAY Golden Aura Melting Souffle Moisturizer | 52.13 | 124.93 | 174.90 | 258.91 | 84.01 | 2.07* |
| OLAY REGENERIST Micro-Sculpting Cream | 52.13 | 176.27 | 246.78 | 288.08 | 41.30 | 1.63* |
| OLAY REGENERIST CELLSCIENCE Anti-Aging Cream | 52.13 | 146.17 | 204.64 | 173.79 | −30.85 | 1.19 |

*p < 0.05 vs. second composition penetration alone

Example 3—Thermodynamic Potential

This example qualitatively illustrates why applying skin care products according to the present regimen should yield lower skin penetration results. In basic terms, the thermodynamic potential for a vitamin $B_3$ to penetrate into the skin from a skin care composition is directly proportional to the concentration of the vitamin $B_3$ compound in the composition. In other words, the thermodynamic potential of the vitamin $B_3$ compound can be expressed as a ratio of vitamin $B_3$ concentration to product mass. And when two composition of differing concentrations of vitamin $B_3$ compound are combined on the skin during a regimen, there is a dilution effect, which should decrease in the thermodynamic potential of the combined compositions relative to the higher concentration composition. This effect is summarized in Table 3 below, which relies on the measured skin penetration of the test compositions from Example 2. As illustrated in Table 3, the skin penetration of the niacinamide applied in the regimen is unexpectedly high.

TABLE 3

| Composition | % niacinamide | Total product (mg) | Thermodynamic potential | Expected penetration | Actual penetration |
|---|---|---|---|---|---|
| Composition I | 2% | 5 | 0.4 | Low | Low |
| Second Skin Care composition | 5% | 5 | 1 | High | High |
| Regimen | 7% (2% + 5%) | 10 (5% + 5%) | 0.7 | Medium | High |

Example 4—Opacity

This example demonstrates the desired opacity properties of the present low-pH compositions. An opacity of between 15 than 75 is generally desired. If the opacity is lowering than 15, the composition appears to much like water and consumers may question its efficacy. But if the opacity is greater than 75, consumers may assume that the composition is thick, tacky, and/or that it won't penetrate the skin. Compositions J, M, N, P, Q R, S, and T were tested in this example. In addition, the opacity of a conventional skin care composition (C1) was also tested. The conventional composition is Example 1 of U.S. Pat. No. 5,968,528 to Deckner, et al. The results of the test are summarized in Table 4. As can be seen in Table 4, compositions that are completely free of oil (i.e., compositions J and R) do not provide enough opacity, and compositions that are not tailored to balance the amount of oil and thickener, skin care active and/or buffer system may be too opaque, as demonstrated by composition C1.

TABLE 4

| Composition | J | R | M | N | P | Q | S | T | C1 |
|---|---|---|---|---|---|---|---|---|---|
| Opacity | 6 | 6 | 37 | 66 | 31 | 58 | 33 | 30 | 84 |

Example 5—Low Irritation

This Example demonstrates the low irritation potential of the present low-pH composition. The low-pH composition was tested in a clinical study, an in vitro cell-based assay and an in vivo human study to determine the relative irritation potential of the composition.

Clinical Study

As part of the clinical study described in Example 3 above, test subjects were asked to fill out a questionnaire that rated the level of irritancy associated with the test products that were applied to their skin. The questionnaire asked the test subjects to rate their test products for "Not Irritating the Skin." The questionnaire provided 7 possible answers: 1) Strongly Agree; 2) Agree; 3) Slightly Agree; 4) Don't Know; 5) Slightly Disagree; 6) Disagree; and 7) Strongly Disagree. The test compositions used in this Example are Compositions G and I from Table 1 and the vehicle control from Example 3. The results of the test at week 4 and week 8 are summarized below in Table 5. "Top 3" refers to the percent of test subjects who answered "Strongly Agree," "Agree," and "Slightly Agree."

TABLE 5

| Week | Treatment | Top 3 |
| --- | --- | --- |
| 4 | Vehicle Control | 97% |
| 4 | Composition I | 98% |
| 4 | Composition G | 97% |
| 8 | Vehicle Control | 98% |
| 8 | Composition I | 100% |
| 8 | Composition G | 100% |

At week 4, 98% of test subjects agreed that the inventive compositions did not irritate the skin versus 97% who agreed that the vehicle control did not irritate the skin. At week 8, 100% of the test subjects agreed that the test compositions did not irritate the skin compared to 98% who agreed that the vehicle control did not irritate the skin. Thus, the results of this test suggest that that present low-pH compositions can improve the appearance of skin without irritating the skin of the user.

In Vitro Study

The in vitro portion of this example examines the ability of a test composition to activate the well-known TRPV1 sensory receptor in commercially available HEK293 cells. TRP receptors (e.g., TRPA1, TRPV1 and TRPM8) are sensory receptors known for their involvement in communicating thermal sensations (i.e., hot and cold) to the central nervous system. TRPV1 is also believed to be involved in triggering skin sensorial irritations such as itching, burning, pain, tingling, stinging and inflammation. Specific human TRPV1 receptor expressing cell lines have previously been used to evaluate the ability of a material or composition to activate TRPV1, especially for evaluating the burning, tingling, taste sensation and/or pain relief effects of various consumer product formulations. In this example, HEK293 cells are pre-loaded with Fluo-4 AM, which is a calcium binding dye, and treated with control substances and test compositions in a high throughput manner using a FLIPR TETRA brand cellular screening system (available from Molecular Devices, LLC) or equivalent. Upon TRPV1 ion channel activation, calcium ions enter the cells and bind the Fluo-4 dye, producing a fluorescent signal, allowing quantification of the response. To reduce the impact of non-specific calcium mobilization unrelated to TRPV1 activation, formula responses are measured in the presence and absence of a specific TRPV1 inhibitor/antagonist compound. Positive signal of TRPV1 receptor activation by formula will disappear or be reduced in the presence of specific antagonists, thereby increasing the accuracy of data collection ascribed to formula-dependent TRPV1 activation.

TRPV1 Assay

To begin the assay, HEK293 cells are grown in DMEM media containing 10% FBS, high glucose, L-glutamine, phenol red, 100 ug/ml G418, and sodium pyruvate at 33° C. and 5% $CO_2$ for 4-5 days (80-90% confluent) (see, e.g., Sadofsky, L. R., et al. *Unique Responses are Observed in Transient Receptor Potential Ankyrin* 1 *and Vanilloid* 1 (*TRPA*1 *and TRPV*1) *Co-Expressing Cells. Cells* 2014, 3, 616-626). Cells at second passage are removed from the tissue culture vessel with PBS and the detached cells are spun in a centrifuge at low speed (800-1000 rpm) for 3 min to form a pellet. The PBS medium is removed and the cell pellet is resuspended in 4 mL growth medium. 50 µg of Fluo-4 AM calcium dye dissolved in 25 µL Pluronic F-127 is added and then the cells are incubated at room temperature for 1 hour with gentle shaking. The cells are washed once with 45 mL assay buffer (1×HBSS, 20 mM HEPES) by low speed centrifugation (800-1000 rpm) for 3 minutes and then re-suspended in 10 mL of the assay buffer. Dispense 100 µL aliquots (approximately $15 \times 10^4$ cells) in each well of a 96-well, black, flat-bottom plate. Let the plates sit at room temperature for 30 minutes and then record baseline fluorescence using the cellular screening system (e.g., FLIPR TETRA or equivalent) at $\lambda_{ex}$ 488 nm and $\lambda_{em}$ 514 nm. Capsaicin (350 nM) is used as the agonist control for each plate and ionomycin (2 uM) is used as the positive control.

Test samples are prepared as a 12× (10.8% formula) stock in assay buffer (w/v) and allowed to sit at room temperature for 1 hour. The test samples are then centrifuged at 14,000 rpm for 3 minutes. The aqueous phase is removed from the centrifuged sample and placed in a suitable tube and mix 1:1 in assay buffer to create a 6× stock. Prepare the TRPV1 antagonist composition by mixing the separated aqueous phase 1:1 with a 12× stock of the capsazepine (25 uM final concentration). Dilute the 6× samples 1:3 with assay buffer or 6× stock of the TRPV1 antagonist capsazepine (25 uM). Add 20 µL of the diluted composition to 96 well plates wells in triplicate for a final dilution of 0.3% formula.

Figure 3:
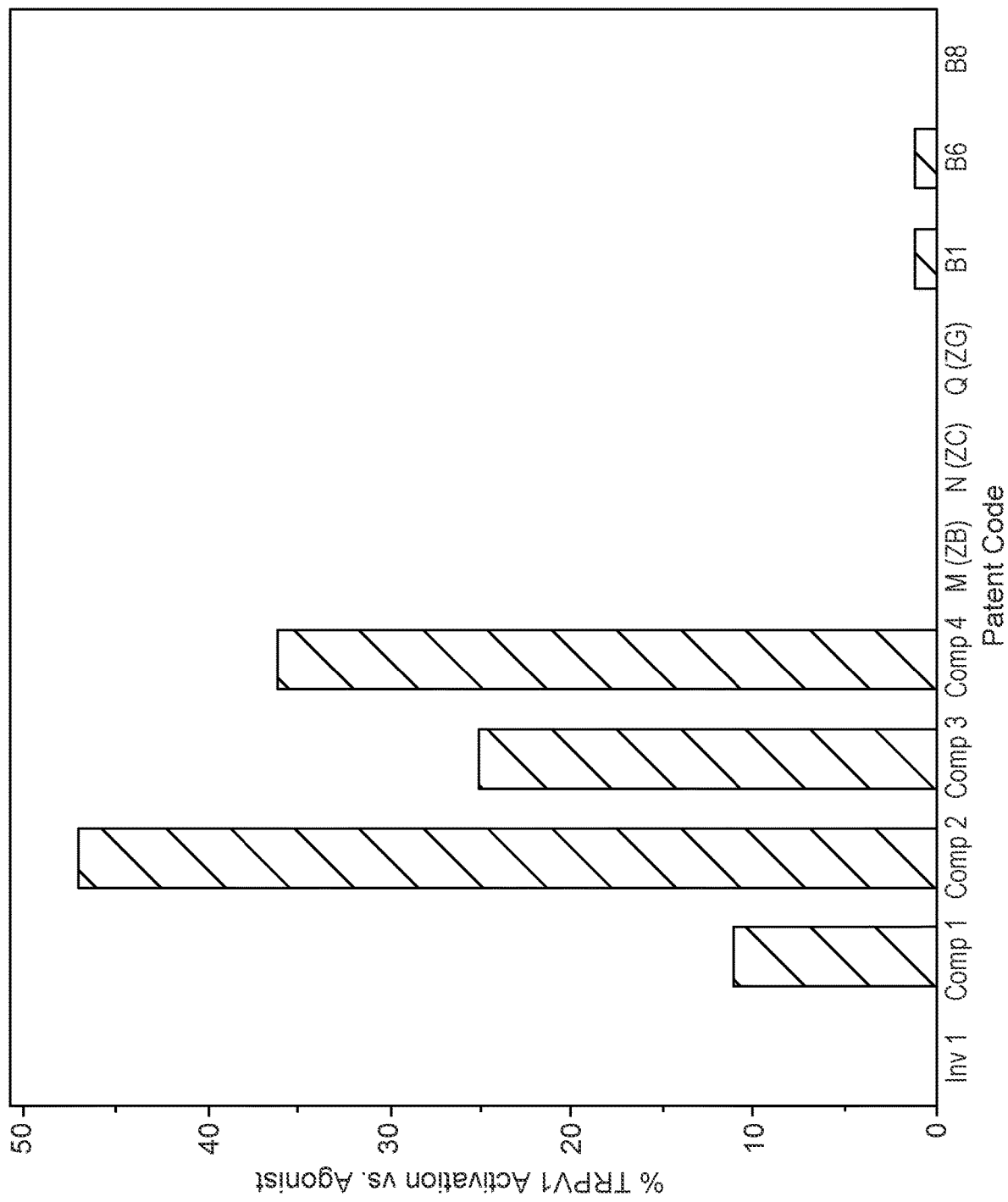
FIG. 3 illustrates the results of the in vitro low irritation testing.

The maximum fluorescence value in each well up to the time of the peak agonist control response is recorded (typically 40-50 seconds). Values of replicate wells are averaged and then converted to a percentage of the capsaicin agonist control response. Each test sample response is reported as the difference between the (mean test sample response)−(mean test sample response+antagonist). Responses that fall below zero are reported as "no response". Compositions M, N, and Q from Table 1 were tested in this example. The compositions shown below in Tables 6A and 6B were also tested. The results of the testing are summarized in Table 6C and illustrated in FIG. 3, which shows, among other things, that the lactic acid/sodium lactate buffer system of the Inventive composition exhibited significantly less TRPV1 activation than the Comparative low-pH compositions. In particular, the inventive composition exhibited less than 10% TRPV1 activation versus the agonist control.

TABLE 6A

| Ingredients | Inventive 1 2.4% Lactate buffer | Inventive 2 5% Gluconate buffer | Comparative 1 3% Citate buffer | Comparative 2 4% citrate buffer | Comparative 3 L'Oreal Revitalift Derm Intensives 10% Pure Glycolic Acid Serum | Comparative 4 Neostrata Resurface Glycolic Renewal Smoothing Cream 10% AHA |
|---|---|---|---|---|---|---|
| | | | | | Ingredient percentages not available | |
| Purified Water | 84.170 | 82.070 | 84.270 | 79.195 | | |
| D-Panthenol | 0.500 | 0.500 | 0.500 | 1.000 | | |
| Sodium Benzoate | 0.050 | 0.050 | 0.050 | 0.100 | | |
| Phenoxyethanol | 0.250 | 0.250 | 0.250 | 0.375 | | |
| Disodium EDTA | 0.100 | 0.100 | 0.100 | | | |
| 1,2-Hexanediol and 1,2-Octanediol[1] | | | | 0.800 | | |
| Niacinamide | 2.000 | 2.000 | 2.000 | 5.000 | | |
| Glycerin | 3.000 | 3.000 | 3.000 | 5.000 | | |
| Xylitol | 1.400 | 1.400 | 1.400 | 3.000 | | |
| Trehalose | 0.100 | 0.100 | 0.100 | — | | |
| 90% L-Lactic acid[2] | 1.800 | — | — | — | | |
| 60% Sodium L lactate[3] | 1.300 | — | — | — | | |
| Citric acid | — | — | 1.950 | 3.800 | | |
| Sodium Citrate | — | — | 1.050 | 0.200 | | |
| Glucono delta lactone | — | 2.900 | — | — | | |
| Sodium gluconate | — | 2.300 | — | — | | |
| Polyacrylate crosspolymer-6[4] | 1.200 | 1.200 | 1.200 | 1.500 | | |
| Dimethicone 5cst | 4.000 | 4.000 | 4.000 | — | | |
| KF-6011P[5] | 0.100 | 0.100 | 0.100 | — | | |
| Perfume | 0.030 | 0.030 | 0.030 | 0.030 | | |
| TOTAL | 100.000 | 100.000 | 100.000 | 100.000 | | |
| pH | 3.81 | 3.83 | 3.85 | 3.51 | 3.95 | 3.61 |

[1]SYMDIOL 68 available from Symrise
[2]PURAC HIPURE 90 available from Corbion
[3]PURASAL S HQ-60 available from Corbion
[4]SEPIMAX ZEN available from Seppic
[5]KF-6011P available from Shin-Etsu

TABLE 6B

| Ingredients | B1 % | B6 % | B8 % |
|---|---|---|---|
| Water | qs | qs | qs |
| Glycerin | 5.0 | 5.0 | 5.0 |
| Dimethicone 5 cSt | 4.0 | 4.0 | 4.0 |
| Niacinamide | 2.0 | 2.0 | 2.0 |
| Lactic acid[1] | — | 1.62 | 1.62 |
| Sodium lactate[2] | — | 0.78 | 0.78 |
| Glucono delta lactone[3] | 3.1 | 3.1 | — |
| Sodium Gluconate[3] | 1.8 | 1.8 | — |
| Mandelic acid | — | — | — |
| Polyacrylate crosspolymer-6[4] | 1.2 | 1.2 | 1.5 |
| Panthenol | 0.5 | 0.5 | 0.5 |
| Disodium EDTA | 0.1 | 0.1 | 0.1 |
| PEG-11 methylether dimethicone[5] | 0.1 | 0.1 | 0.1 |
| Trehalose | 0.1 | 0.1 | 0.1 |
| Sodium Benzoate | 0.05 | 0.05 | 0.05 |
| TOTAL | 100.0 | 100.0 | 100.0 |
| pH | 3.95 | 3.65 | 3.80 |

[1]PURAC HIPURE 90 available from Corbion
[2]PURASAL S HQ-60 available from Corbion
[3]Available from Jungbunzlauer
[4]SEPIMAX ZEN available from Seppic
[5]KF-6011P available from Shin-Etsu

TABLE 6C

| Composition | Inv 1 | Comp 1 | Comp 2 | Comp 3 | Comp 4 | M | N | Q | B1 | B6 | B8 |
|---|---|---|---|---|---|---|---|---|---|---|---|
| TRPV1 % activation vs. control | 0 | 11 | 47 | 25 | 36 | 0 | 0 | 0 | 1.2 | 1.35 | 0 |

In Vivo Study

The in vivo portion of this example illustrates the low irritation potential of the present compositions relative to comparative low pH formulations that use a different buffering system. This study was a single product, blinded test using female test subjects aged 25-54. The test subjects were asked to apply approximately 0.5 g (i.e., 1 pump) of the test composition to their entire face twice per day (morning and night). The compositions tested in this study are provided in Table 6A above. After 1 week of use, the test subjects were asked whether the test composition was irritating to the skin. The results of the in vivo study are summarized in Table 7 below. As can be seen in Table 7, the data suggest that the inventive examples are less irritating to the skin versus the two comparative examples.

TABLE 7

|  | Inventive 1 | Inventive 2 | Comparative 1 | Comparative 2 |
| --- | --- | --- | --- | --- |
| Not Irritating Skin | 84.0% | 86.3% | 77% | 49.1% |

Examples/Combinations

A. A method of improving skin penetration of a vitamin $B_3$ compound, comprising:
  identifying a target portion of skin where a skin health or appearance benefit is desired;
  applying a low-pH skin care composition to the target portion of skin, wherein the low-pH skin care composition comprises a first concentration of a vitamin $B_3$ compound; and
  thereafter applying a second skin care composition to the target portion of skin, wherein the second skin care composition comprises a second concentration of the vitamin $B_3$ compound, and the second concentration is higher than the first concentration.

B. The method of paragraph A, wherein the low-pH composition has a pH of between about 2.0 and about 5.0, preferably about 2.5 to about 4.5, and more preferably about 3.0 to about 4.3.

C. The method of any preceding paragraph, wherein the second skin care composition has a pH of about 5.0 to about 8.0.

D. The method of any preceding paragraph, wherein the vitamin $B_3$ compound is selected from the group consisting of niacinamide, nicotinic acid, nicotinyl alcohol, derivatives of these, and combinations thereof.

E. The method of paragraph D, wherein the vitamin $B_3$ compound is niacinamide

F. The method of paragraph D, wherein the low-pH composition comprises about 0.01% to about 3%, by weight, of the vitamin $B_3$ compound.

G. The method of paragraph D, wherein the second skin care composition comprises about 2% to about 10%, by weight, of the vitamin $B_3$ compound.

H. The method of any preceding paragraph, wherein the low-pH buffer system comprises an acid buffering agent selected from lactic acid, gluconic acid, lactobionic acid, and maltobionic acid and a salt buffering agent selected from sodium lactate, sodium gluconate, calcium lactate gluconate, and potassium gluconate.

I. The method of any preceding paragraph, wherein the weight % ratio of vitamin $B_3$ compound in the low-pH composition to vitamin $B_3$ compound in the second skin care composition is about 1:10 to about 3:4, preferably about 1:5 to about 1:2.

J. The method of any preceding paragraph, wherein the low-pH composition comprises:
  a) about 0.1% to 5% of a pH buffering system comprising an acid buffering agent and a salt buffering agent;
  b) about 0.1% to 5% of a polymer thickener comprising a low-pH tolerant thickener; and
  c) about 0.1% to 10% of a tack-reducing oil having a viscosity of 100 cSt or less at 25° C.

K. The method of paragraph J, wherein the tack-reducing oil is a silicone oil, preferably dimethicone.

L. The method of any preceding paragraph, wherein the low-pH composition further comprises about 0.01% to about 1% of a silicone emulsifier.

M. The method of any preceding paragraph, wherein at least one of the first and second skin care compositions comprises an additional skin care active selected from the group consisting of vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, and combinations thereof.

N. The method of any preceding paragraph, wherein the skin care composition has an Opacity of about 15 to about 75, preferably about 35 to about 60 according to the Opacity Test.

O. The method of any preceding paragraph, wherein the low-pH composition exhibits a TRPV1 activation of less than about 10%, preferably less than about 5%, according to the TRPV1 assay.

P. The method of any preceding paragraph, wherein the low-pH composition is a skin care essence product that has a viscosity of about 1 cP to about 30000 cP at 25° C., preferably about 1000 cP to about 15000 cP.

Q. The method of any preceding paragraph, wherein the applying the low-pH skin care composition and the second skin care composition over the course of the treatment period does not result in skin irritation to the target portion of skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving skin penetration of a vitamin $B_3$ compound, comprising:
   identifying a target portion of skin where a skin health or appearance benefit is desired;
   applying a low-pH skin care composition to the target portion of skin, wherein the low-pH skin care composition comprises a first concentration of a vitamin $B_3$ compound and a pH less than 5; and
   thereafter applying a second skin care composition to the target portion of skin, wherein the second skin care composition comprises a second concentration of the vitamin $B_3$ compound, and the second concentration is higher than the first concentration.

2. The method of claim 1, wherein the low-pH skin care composition has a pH of between about 2.0 and about 4.5.

3. The method of claim 2, wherein the low-pH skin care composition has a pH of between about 2.5 and about 4.0.

4. The method of claim 1, wherein the second skin care composition has a pH of about 5.0 to about 8.0.

5. The method of claim 1, wherein the vitamin $B_3$ compound is selected from the group consisting of niacinamide, nicotinic acid, nicotinyl alcohol, derivatives thereof, and combinations thereof.

6. The method of claim 5, wherein the vitamin $B_3$ compound is niacinamide.

7. The method of claim 5, wherein the low-pH skin care composition comprises about 0.01% to about 3%, by weight, of the vitamin $B_3$ compound.

8. The method of claim 5, wherein the second skin care composition comprises about 2% to about 10%, by weight, of the vitamin $B_3$ compound.

9. The method of claim 1, wherein the low-pH skin care composition further comprises a buffer system comprising one or more acid buffering agents comprising lactic acid, gluconic acid, lactobionic acid, and maltobionic acid and a salt buffering agent selected from sodium lactate, sodium gluconate, calcium lactate gluconate, zinc lactate, potassium lactate, potassium gluconate, or a combination thereof.

10. The method of claim 1, wherein a weight % ratio of vitamin $B_3$ compound in the low-pH skin care composition to vitamin $B_3$ compound in the second skin care composition is about 1:10 to about 3:4.

11. The method of claim 9, wherein a weight % ratio of vitamin $B_3$ compound in the low-pH skin care composition to vitamin $B_3$ compound in the second skin care composition is about 1:5 to about 1:2.

12. The method of claim 1, wherein the low-pH skin care composition comprises:
   a) about 0.1% to 5% of a pH buffering system comprising an acid buffering agent and a salt buffering agent;
   b) about 0.1% to 5% of a polymer thickener comprising a low-pH tolerant thickener; and
   c) about 0.1% to 10% of a tack-reducing oil having a viscosity of 100 cSt or less at 25° C.

13. The method of claim 12, wherein the tack-reducing oil is a silicone oil that has a viscosity of 100 cSt or less at 25° C.

14. The method of claim 13, wherein the silicone oil has a viscosity of 10 cSt or less.

15. The method of claim 9, wherein the low-pH composition further comprises about 0.01% to about 1% of a silicone emulsifier.

16. The method of claim 1, wherein at least one of the low-pH skin care composition and the second skin care compositions comprises an additional skin care active selected from the group consisting of vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, and combinations thereof.

17. The method of claim 1, wherein the low-pH skin care composition has an Opacity of about 15 to about 75, according to the Opacity Test.

18. The method of claim 1, wherein the low-pH skin care composition exhibits a TRPV1 activation of less than about 10% according to the TRPV1 assay.

19. The method of claim 1, wherein the low-pH skin care composition is a skin care essence product that has a viscosity of about 1 cP to about 30000 cP at 25° C.

20. The method of claim 1, wherein the applying the low-pH skin care composition and the second skin care composition over the course of the treatment period does not result in skin irritation to the target portion of skin.

* * * * *